United States Patent
Jacobsen et al.

(10) Patent No.: US 9,226,689 B2
(45) Date of Patent: Jan. 5, 2016

(54) FLEXIBLE CIRCUIT SHEET

(71) Applicant: Medtronic Xomed, Inc., Jacksonville, FL (US)

(72) Inventors: Brad Jacobsen, Erie, CO (US); Bruce M. Burg, Louisville, CO (US); Orey G. Block, Westminster, CO (US); Andrew Bzostek, Boulder, CO (US); Vince J. Doerr, Boulder, CO (US); Abhishek Jain, Centennial, CO (US); Brandon Merkl, Lakewood, CO (US); Joseph Thomas Cilke, Broomfield, CO (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 52 days.

(21) Appl. No.: 13/751,032

(22) Filed: Jan. 25, 2013

(65) Prior Publication Data

US 2014/0012130 A1 Jan. 9, 2014

Related U.S. Application Data

(63) Continuation-in-part of application No. 13/748,150, filed on Jan. 23, 2013, which is a continuation-in-part of application No. 13/097,243, filed on Apr. 29, 2011, and a continuation-in-part of application No.

(Continued)

(51) Int. Cl.
*A61B 5/055* (2006.01)
*A61B 5/06* (2006.01)
(Continued)

(52) U.S. Cl.
CPC ............. *A61B 5/065* (2013.01); *A61B 19/5244* (2013.01); *H05K 1/028* (2013.01);
(Continued)

(58) Field of Classification Search
CPC ............... A61B 5/065; A61B 19/5244; A61B 2019/5251; A61B 2019/547; A61B 2019/5483; A61B 2017/00946; A61B 2017/24; H05K 1/0298; H05K 1/028; H05K 2201/056; A61M 1/008; A61M 2205/3561; A61M 2205/3576
USPC .......................................................... 600/424
See application file for complete search history.

(56) References Cited

U.S. PATENT DOCUMENTS 4,317,078 A 2/1982 Weed et al.
4,788,987 A 12/1988 Nickel
(Continued)

FOREIGN PATENT DOCUMENTS

AU 2011245296 A1 12/2012
CA 2797359 A1 11/2011
(Continued)

OTHER PUBLICATIONS http://oxforddictionaries.com/definition/english/barrel (accessed Dec. 3, 2012).
(Continued)

*Primary Examiner* — Long V Le
*Assistant Examiner* — Angela M Hoffa
(74) *Attorney, Agent, or Firm* — Harness, Dickey

(57) ABSTRACT

A surgical instrument is disclosed having an elongated body portion having a proximal end and a distal end. The body portion is formed from a plastically deformable material such that the body portion can be bent between the proximal and distal ends from a first configuration to a second bent configuration and maintains the bent configuration. A flexible circuit having at least a pair of lead wires disposed around the body portion. The pair of lead wires are configured to conform to the bent configuration of the body portion such that they do not break during bending of the body portion. A tracking device adapted to cooperate with a navigation system to track the distal end of the instrument is coupled to the flexible circuit.

41 Claims, 25 Drawing Sheets

Related U.S. Application Data

12/400,951, filed on Mar. 10, 2009, now Pat. No. 8,504,139.

(60) Provisional application No. 61/330,024, filed on Apr. 30, 2010.

(51) Int. Cl.

| | | |
|---|---|---|
| *H05K 1/02* | (2006.01) | |
| *A61B 19/00* | (2006.01) | |
| *A61M 1/00* | (2006.01) | |
| *A61B 17/24* | (2006.01) | |
| *A61B 17/00* | (2006.01) | |

(52) U.S. Cl.
CPC .............. *H05K 1/0298* (2013.01); *A61B 17/24* (2013.01); *A61B 2017/00946* (2013.01); *A61B 2019/5251* (2013.01); *A61B 2019/547* (2013.01); *A61B 2019/5483* (2013.01); *A61M 1/008* (2013.01); *A61M 2205/3561* (2013.01); *A61M 2205/3576* (2013.01); *H05K 2201/056* (2013.01); *H05K 2201/2027* (2013.01)

(56) References Cited

U.S. PATENT DOCUMENTS

| | | | |
|---|---|---|---|
| 4,806,182 A | 2/1989 | Rydell et al. | |
| 5,005,592 A | 4/1991 | Cartmell | |
| 5,226,423 A | 7/1993 | Tenerz et al. | |
| 5,391,199 A | 2/1995 | Ben-Haim | |
| 5,443,489 A | 8/1995 | Ben-Haim | |
| 5,591,141 A | 1/1997 | Nettekoven | |
| 5,592,939 A | 1/1997 | Martinelli | |
| 5,740,808 A | 4/1998 | Panescu et al. | |
| 5,762,637 A | 6/1998 | Berg et al. | |
| 5,840,024 A | 11/1998 | Taniguchi et al. | |
| 5,913,820 A | 6/1999 | Bladen et al. | |
| 5,938,602 A | 8/1999 | Lloyd | |
| 5,963,120 A | 10/1999 | Zaviska | |
| 5,983,126 A | 11/1999 | Wittkampf | |
| 6,021,343 A | 2/2000 | Foley et al. | |
| 6,106,486 A | 8/2000 | Tenerz et al. | |
| 6,201,387 B1 | 3/2001 | Govari | |
| 6,235,038 B1 | 5/2001 | Hunter et al. | |
| 6,253,770 B1 | 7/2001 | Acker et al. | |
| 6,254,600 B1 | 7/2001 | Willink et al. | |
| 6,332,891 B1 | 12/2001 | Himes | |
| 6,336,906 B1 | 1/2002 | Hammarstrom et al. | |
| 6,348,058 B1 | 2/2002 | Melkent et al. | |
| 6,381,485 B1 | 4/2002 | Hunter et al. | |
| 6,427,079 B1 | 7/2002 | Schneider et al. | |
| 6,434,507 B1 | 8/2002 | Clayton et al. | |
| 6,474,341 B1 | 11/2002 | Hunter et al. | |
| 6,478,802 B2 | 11/2002 | Kienzle, III et al. | |
| 6,556,857 B1 | 4/2003 | Estes et al. | |
| 6,610,066 B2 | 8/2003 | Dinger et al. | |
| 6,615,155 B2 | 9/2003 | Gilboa | |
| 6,616,651 B1 | 9/2003 | Stevens | |
| 6,687,531 B1 | 2/2004 | Ferre et al. | |
| 6,689,049 B1 | 2/2004 | Miyagi et al. | |
| 6,695,764 B2 | 2/2004 | Silverman et al. | |
| 6,747,539 B1 | 6/2004 | Martinelli | |
| 6,796,988 B2 | 9/2004 | Melkent et al. | |
| 6,833,814 B2 | 12/2004 | Gilboa et al. | |
| 6,926,674 B2 | 8/2005 | Tenerz et al. | |
| 6,940,941 B2 | 9/2005 | Gregerson et al. | |
| 6,977,575 B2 | 12/2005 | Bernier | |
| 6,980,849 B2 | 12/2005 | Sasso | |
| 6,993,374 B2 | 1/2006 | Sasso | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,118,378 B1 | 10/2006 | Karapetyan | |
| 7,166,114 B2 | 1/2007 | Moctezuma De La Barrera et al. | |
| 7,188,998 B2 | 3/2007 | Gregerson et al. | |
| 7,226,456 B2 | 6/2007 | O'Neil et al. | |
| 7,346,417 B2 | 3/2008 | Luth et al. | |
| 7,366,562 B2 | 4/2008 | Dukesherer et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,537,594 B2 | 5/2009 | Sartor | |
| 7,559,137 B2 | 7/2009 | Beer et al. | |
| 7,604,609 B2 | 10/2009 | Jervis | |
| 7,625,617 B1 | 12/2009 | Anderson et al. | |
| 7,629,015 B2 | 12/2009 | Anderson et al. | |
| 7,637,896 B2 | 12/2009 | Voegele et al. | |
| 7,647,083 B2* | 1/2010 | Al-Ali et al. | 600/310 |
| 7,697,972 B2 | 4/2010 | Verard et al. | |
| 7,751,865 B2 | 7/2010 | Jascob et al. | |
| 7,763,035 B2 | 7/2010 | Melkent et al. | |
| 7,774,933 B2 | 8/2010 | Wilson et al. | |
| 7,797,032 B2 | 9/2010 | Martinelli et al. | |
| 7,818,044 B2 | 10/2010 | Dukesherer et al. | |
| 7,840,253 B2 | 11/2010 | Tremblay et al. | |
| 7,844,319 B2* | 11/2010 | Susil et al. | 600/411 |
| 7,971,341 B2 | 7/2011 | Dukesherer et al. | |
| 7,979,032 B2 | 7/2011 | Lomnitz | |
| 8,075,969 B2* | 12/2011 | Anderson et al. | 428/36.9 |
| 8,086,298 B2 | 12/2011 | Whitmore, III et al. | |
| 8,105,339 B2 | 1/2012 | Melkent et al. | |
| 8,147,486 B2* | 4/2012 | Honour et al. | 606/41 |
| 8,239,001 B2 | 8/2012 | Verard et al. | |
| 8,251,949 B2 | 8/2012 | Warnack | |
| 8,255,027 B2* | 8/2012 | Al-Ali et al. | 600/310 |
| 8,504,139 B2 | 8/2013 | Jacobsen et al. | |
| 8,644,907 B2 | 2/2014 | Hartmann et al. | |
| 8,648,605 B2 | 2/2014 | Nakamura et al. | |
| 8,674,694 B2* | 3/2014 | Hyde et al. | 324/316 |
| 8,862,204 B2* | 10/2014 | Sobe et al. | 600/424 |
| 2001/0034549 A1 | 10/2001 | Bartholf et al. | |
| 2002/0165448 A1 | 11/2002 | Ben-Haim et al. | |
| 2003/0050552 A1* | 3/2003 | Vu | 600/410 |
| 2003/0187347 A1 | 10/2003 | Nevo et al. | |
| 2004/0116803 A1 | 6/2004 | Jascob et al. | |
| 2004/0199072 A1 | 10/2004 | Sprouse et al. | |
| 2004/0215071 A1 | 10/2004 | Frank et al. | |
| 2005/0027339 A1 | 2/2005 | Schrom et al. | |
| 2005/0027340 A1 | 2/2005 | Schrom et al. | |
| 2005/0027341 A1 | 2/2005 | Schrom et al. | |
| 2005/0060885 A1 | 3/2005 | Johnson et al. | |
| 2005/0085715 A1 | 4/2005 | Dukesherer et al. | |
| 2005/0085720 A1 | 4/2005 | Jascob et al. | |
| 2005/0105212 A1 | 5/2005 | Sato | |
| 2005/0154294 A1 | 7/2005 | Uchiyama et al. | |
| 2005/0171508 A1 | 8/2005 | Gilboa | |
| 2005/0215922 A1 | 9/2005 | Tsonton et al. | |
| 2005/0222554 A1 | 10/2005 | Wallace et al. | |
| 2006/0004286 A1 | 1/2006 | Chang et al. | |
| 2006/0025677 A1 | 2/2006 | Verard et al. | |
| 2006/0036189 A1 | 2/2006 | Martinelli et al. | |
| 2006/0084867 A1 | 4/2006 | Tremblay et al. | |
| 2006/0142656 A1 | 6/2006 | Malackowski et al. | |
| 2006/0206039 A1 | 9/2006 | Wilson et al. | |
| 2006/0206170 A1 | 9/2006 | Denker et al. | |
| 2006/0224142 A1 | 10/2006 | Wilson et al. | |
| 2006/0229624 A1 | 10/2006 | May et al. | |
| 2006/0235314 A1 | 10/2006 | Migliuolo et al. | |
| 2007/0088416 A1* | 4/2007 | Atalar et al. | 607/115 |
| 2007/0157828 A1 | 7/2007 | Susel et al. | |
| 2007/0197899 A1 | 8/2007 | Ritter et al. | |
| 2007/0208252 A1 | 9/2007 | Makower | |
| 2007/0220746 A1 | 9/2007 | Anderson et al. | |
| 2007/0225595 A1 | 9/2007 | Malackowski et al. | |
| 2007/0255132 A1 | 11/2007 | Shalgi et al. | |
| 2008/0097195 A1 | 4/2008 | Urquhart et al. | |
| 2008/0097347 A1 | 4/2008 | Arvanaghi | |
| 2008/0119727 A1 | 5/2008 | Barbagli et al. | |
| 2008/0119919 A1* | 5/2008 | Atalar et al. | 607/116 |
| 2008/0132909 A1 | 6/2008 | Jascob et al. | |
| 2008/0171934 A1 | 7/2008 | Greenan et al. | |

(56) References Cited

U.S. PATENT DOCUMENTS

| | | | |
|---|---|---|---|
| 2008/0171937 A1 | 7/2008 | Dukesherer et al. | |
| 2008/0172069 A1 | 7/2008 | Dukesherer et al. | |
| 2008/0228195 A1 | 9/2008 | von Jako et al. | |
| 2009/0088728 A1 | 4/2009 | Dollar et al. | |
| 2009/0118742 A1 | 5/2009 | Hartmann et al. | |
| 2009/0171187 A1 | 7/2009 | Gerhart et al. | |
| 2009/0204023 A1 | 8/2009 | Goldenberg | |
| 2009/0209947 A1 | 8/2009 | Gordin et al. | |
| 2010/0063383 A1 | 3/2010 | Anderson et al. | |
| 2010/0081965 A1 | 4/2010 | Mugan et al. | |
| 2010/0130852 A1 | 5/2010 | Neidert et al. | |
| 2010/0185083 A1 | 7/2010 | Neidert et al. | |
| 2010/0210939 A1 | 8/2010 | Hartmann et al. | |
| 2010/0228117 A1 | 9/2010 | Hartmann | |
| 2010/0234724 A1 | 9/2010 | Jacobsen et al. | |
| 2010/0253361 A1 | 10/2010 | Nakamura et al. | |
| 2010/0280363 A1 | 11/2010 | Skarda et al. | |
| 2010/0331763 A1 | 12/2010 | Wilson et al. | |
| 2011/0014705 A1 | 1/2011 | Leach et al. | |
| 2011/0060214 A1 | 3/2011 | Makower | |
| 2011/0066029 A1 | 3/2011 | Lyu et al. | |
| 2011/0118592 A1* | 5/2011 | Sobe et al. | 600/424 |
| 2011/0251519 A1 | 10/2011 | Romoscanu | |
| 2011/0258842 A1 | 10/2011 | Dukesherer et al. | |
| 2011/0270081 A1 | 11/2011 | Burg et al. | |
| 2012/0172696 A1* | 7/2012 | Kallback et al. | 600/373 |
| 2012/0197108 A1 | 8/2012 | Hartmann et al. | |
| 2012/0197109 A1 | 8/2012 | Hartmann et al. | |
| 2012/0197110 A1 | 8/2012 | Hartmann et al. | |
| 2012/0245665 A1 | 9/2012 | Friedman et al. | |
| 2012/0283570 A1* | 11/2012 | Tegg | 600/467 |
| 2013/0066194 A1* | 3/2013 | Seter et al. | 600/424 |
| 2013/0137954 A1* | 5/2013 | Jacobsen et al. | 600/373 |
| 2013/0317355 A1 | 11/2013 | Jacobsen et al. | |
| 2014/0012130 A1 | 1/2014 | Jacobsen et al. | |
| 2014/0021213 A1 | 1/2014 | Caplan | |
| 2014/0148692 A1 | 5/2014 | Hartmann et al. | |
| 2014/0158555 A1 | 6/2014 | Nakamura et al. | |
| 2014/0276004 A1 | 9/2014 | Strupeck et al. | |
| 2015/0005625 A1* | 1/2015 | Sobe et al. | 600/424 |

FOREIGN PATENT DOCUMENTS

| | | |
|---|---|---|
| DE | 102009030731 A1 | 12/2010 |
| EP | 0425319 A2 | 5/1991 |
| EP | 1302172 A1 | 4/2003 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2123220 A1 | 11/2009 |
| EP | 2563260 A2 | 3/2013 |
| JP | 03-207344 B2 | 9/2001 |
| JP | 2007-527296 A | 9/2007 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |
| WO | WO-9940856 A1 | 8/1999 |
| WO | WO-0038571 A1 | 7/2000 |
| WO | WO-0134050 A2 | 5/2001 |
| WO | WO-2006096685 A1 | 9/2006 |
| WO | WO-2006116597 A2 | 11/2006 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A1 | 12/2010 |
| WO | WO-2011137301 A2 | 11/2011 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

International Preliminary Report on Patentability mailed Aug. 8, 2013 for PCT/US2012/022676 claiming benefit of U.S. Appl. No. 13/016,740, filed Jan. 28, 2011.

International Preliminary Report on Patentability mailed Aug. 8, 2013 for PCT/US2012/022840 claiming benefit of U.S. Appl. No. 13/016,762, filed Jan. 28, 2011.

International Preliminary Report on Patentability mailed Aug. 8, 2013 for PCT/US2012/022846 claiming benefit of U.S. Appl. No. 13/016,765, filed Jan. 28, 2011.

"Flexible electronics," Dec. 19, 2012, XP055112518, en.wikipedia. org. Retrieved form the Internet: <URL:http://en.wikipedia.org/w/index.php?title=Flexible_electronics&oldid=528841651>[retrieved on Apr. 7, 2014]. (6 sheets).

"Flexible Printed Circuit Manufacturer-Capabilities," Aug. 16, 2012, XP055112534, fpcexpress.com. Retrieved from the Internet: URL: <http://web.archive.org/web/20120816030431/http://fpcexpress.com/capabilities.html>. [retrieved on Apr. 7, 2014][retrieved on May 8, 2014]. (3 sheets).

"Minco Bulletin FC-3," Jul. 31, 2002. XP055115671, Retrieved from the Internet: <URL:http://www.temflexcontrols.com/pdf/fc3.pdf> [retrieved on Apr. 29, 2014]. (1 sheet).

"Sectional design standard for flexible printed boards," Internet Citation, Nov. 30, 1998, pp. 1-35, XP002691487, Retrieved form the Interent: <URL:http://222.184.16.210/smt/tzxt/bz/IPC-2223.pdf>. [retrieved on Feb. 1, 2013].

International Preliminary Report on Patentability and Written Opinion mailed May 8, 2014 for PCT/US2012/061086 claiming benefit of U.S. Appl. No. 13/281,001, filed Oct. 25, 2011.

International Search Report and Written Opinion mailed Apr. 23, 2014 for PCT/US2014/012786 claiming benefit of U.S. Appl. No. 13/748,150, filed Jan. 23, 2013.

International Search Report and Written Opinion mailed May 12, 2014 for PCT/US2014/012967 claiming benefit of U.S. Appl. No. 13/751,032, filed on Jan. 25, 2013.

Examiner's Report dated Dec. 18, 2013 for Canadian Application No. 2,797,359 claiming benefit of U.S. Appl. No. 13/097,243, filed Apr. 29, 2011.

Japanese Office Action dated Jan. 7, 2014 for Japan Application No. 2013-508273 claiming benefit of U.S. Appl. No. 13/097,243, filed Apr. 29, 2011.

"InstaTrak 3500 Plus. Applications: ENT. Cranial." http://www.gehealthcare/usen/xr/surgery/products/nav.html (printed Dec. 14, 2009).

"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"InstaTrak® Image Guided Sinus Surgery, Introduction to the InstaTrak System." Sinus-Clear.com http:/www.sinus-clear.com/instatrak.htm (printed Dec. 14, 2009).

"Mayfield® Skull Clamps and Headrest Systems," Mayfield® Surgical Devices Product Index, pp. 1-6, Dec. 2004 Integra LifeSciences Corporation.

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"The doctor can see you now" brochure. GE Medical Systems (2003) General Electric Company.

"TREON, StealthStation," brochure, Medtronic Surgical Navigation Technologies (2001) 8 pages.

(56) References Cited

OTHER PUBLICATIONS

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

International Preliminary Report on Patentability mailed Nov. 15, 2012 for PCT/US2011/34475 claiming benefit of U.S. Appl. No. 13/097,243, filed Apr. 29, 2011.

International Search Report and Written Opinion mailed Feb. 6, 2013 for PCT/US2012/061086 claiming benefit of U.S. Appl. No. 13/281,001, filed Oct. 25, 2011.

International Search Report and Written Opinion mailed Jul. 6, 2012 for PCT/US2012/022840 claiming benefit to U.S. Appl. No. 13/016,762, filed Jan. 28, 2011.

International Search Report and Written Opinion mailed May 9, 2012 for PCT/US2012/022676 claiming benefit of U.S. Appl. No. 13/016,740, filed Jan. 28, 2011.

International Search Report and Written Opinion mailed May 9, 2012 for PCT/US2012/022846 claiming benefit of U.S. Appl. No. 13/016,765, filed Jan. 28, 2011.

International Search Report and Written Opinion mailed Oct. 31, 2011, claiming benefit of U.S. Appl. No. 13/097,243, filed Apr. 29, 2011.

Invitation to Pay Additional Fees mailed Dec. 17, 2012 for PCT/US2012/061086 claiming benefit of U.S. Appl. No. 13/281,001, filed Oct. 25, 2011.

Invitation to Pay Additional Fees mailed Jul. 25, 2011, claiming benefit of U.S. Appl. No. 13/097,243, filed Apr. 29, 2011.

Invitation to Pay Additional Fees mailed May 8, 2012 for PCT/US2012/022840 claiming benefit of U.S. Appl. No. 13/016,762, filed Jan. 28, 2011.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.

International Preliminary Report on Patentability and Written Opinion mailed Sep. 22, 2011 for PCT/US2010/026655 claiming benefit of U.S. Appl. No. 12/400,451, filed Mar. 10, 2009.

International Search Report and Written Opinion mailed Oct. 27, 2014 for PCT/US2014/028100 claiming benefit of U.S. Appl. No. 14/209,696, filed Mar. 13, 2014.

International Search Report mailed Jul. 15, 2010 for PCT/US2010/026655 claiming benefit of U.S. Appl. No. 12/400,451, filed Mar. 10, 2009.

Invitation to Pay Additional Fees and Where Applicable, Protest Fee mailed Aug. 14, 2014 for PCT/US2014/028100 claiming benefit of U.S. Appl. No. 14/209,696, filed Mar. 13, 2014.

Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.

Communication pursuant to Article 94(3) EPC for European Application No. 12703208.4-1654 dated Apr. 24, 2015.

International Preliminary Report on Patentability and Written Opinion mailed on Aug. 6, 2015 for PCT/US2014/012786 claiming benefit of U.S. Appl. No. 13/748,150 filed on Jan. 23, 2013.

International Preliminary Report on Patentability and Written Opinion mailed on Aug. 6, 2015 for PCT/US2014/012967 claiming benefit of U.S. Appl. No. 13/751,032 filed on Jan. 25, 2013.

International Preliminary Report on Patentability and Written Opinion mailed Sep. 24, 2015 for PCT/US2014/028100 claiming benefit to U.S. Appl. No. 14/209,696 filed Mar. 13, 2014.

International Preliminary Report on Patentability mailed Oct. 27, 2015 for PCT/US2014/034022 claiming benefit of U.S. Appl. No. 13/871,616 filed Apr. 26, 2013.

\* cited by examiner

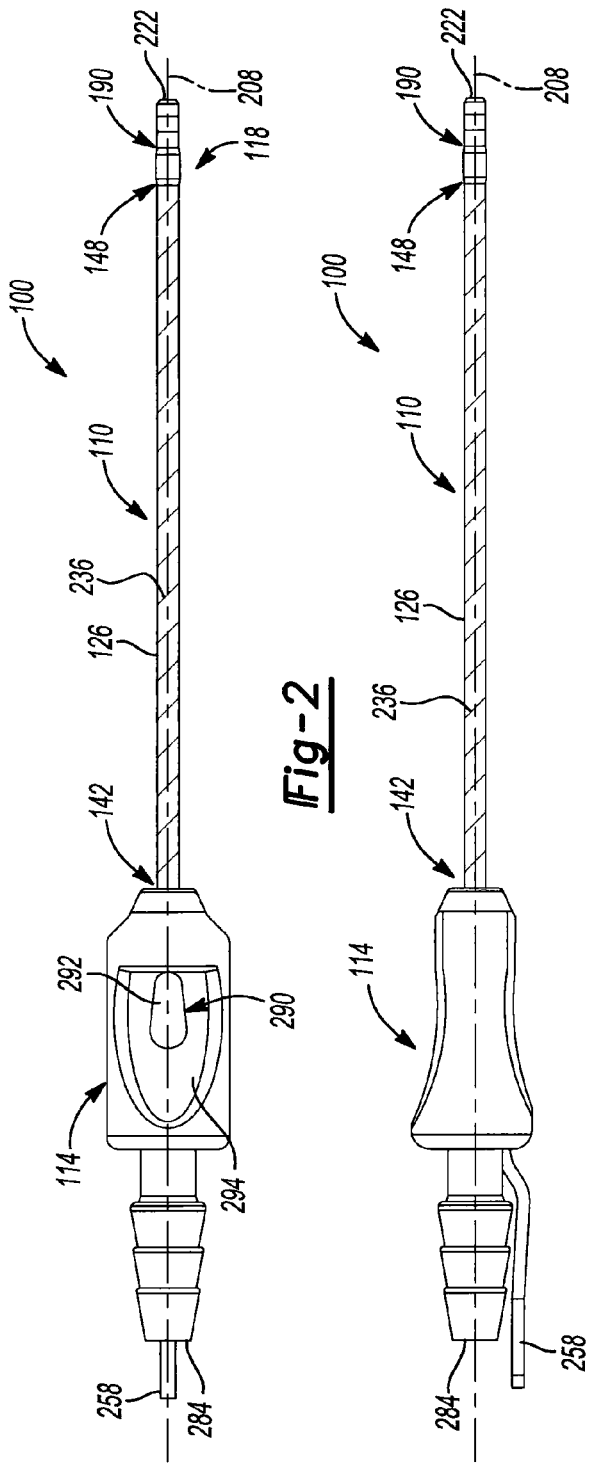
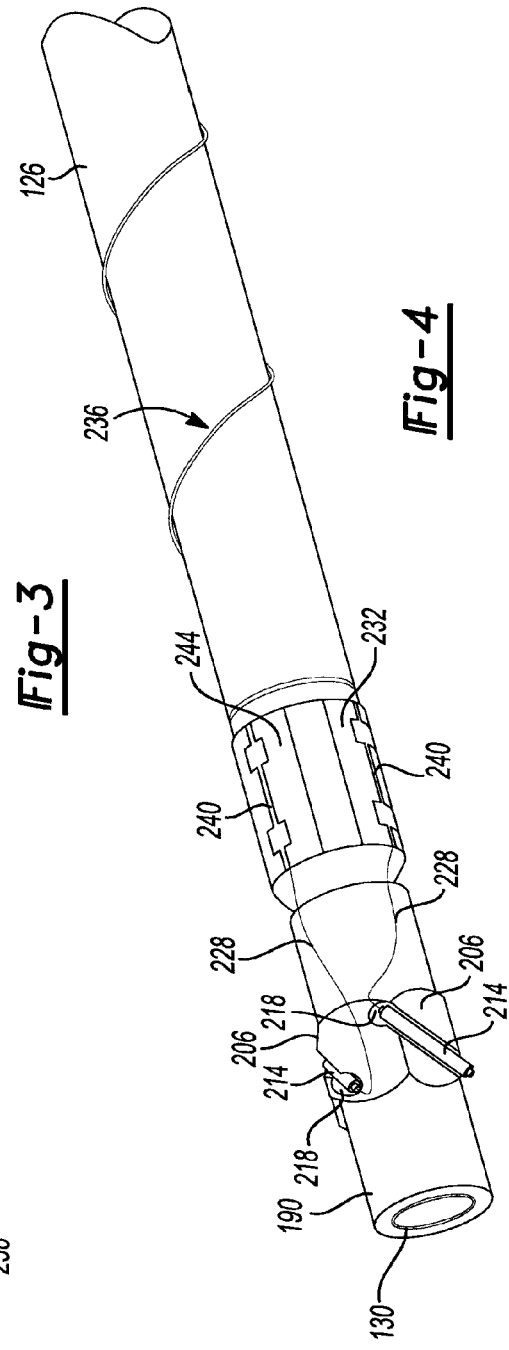

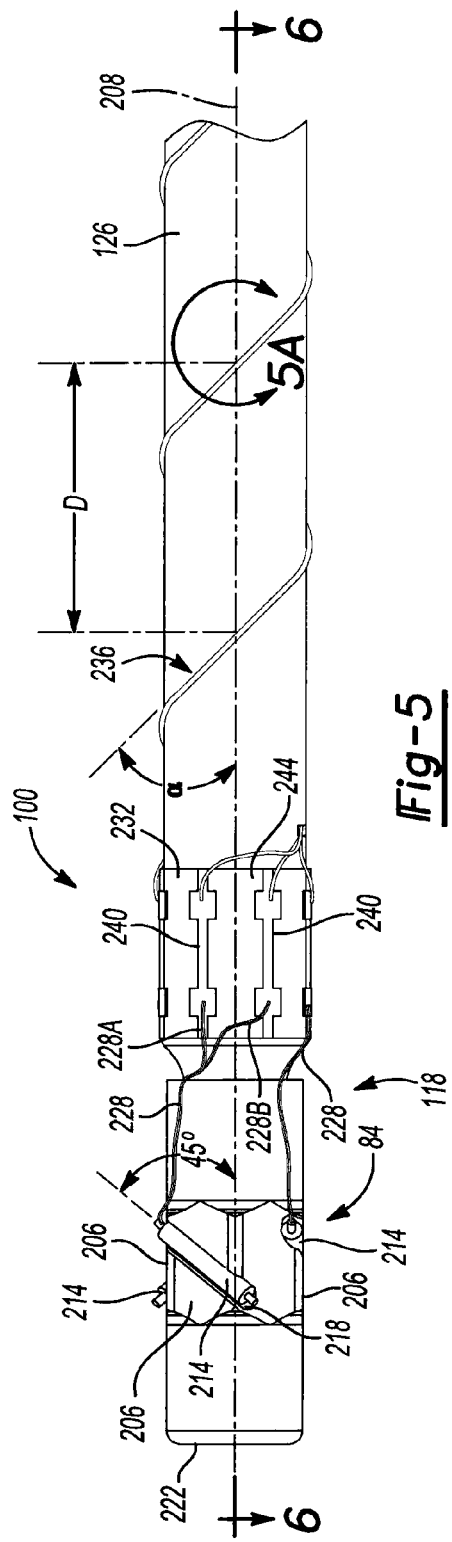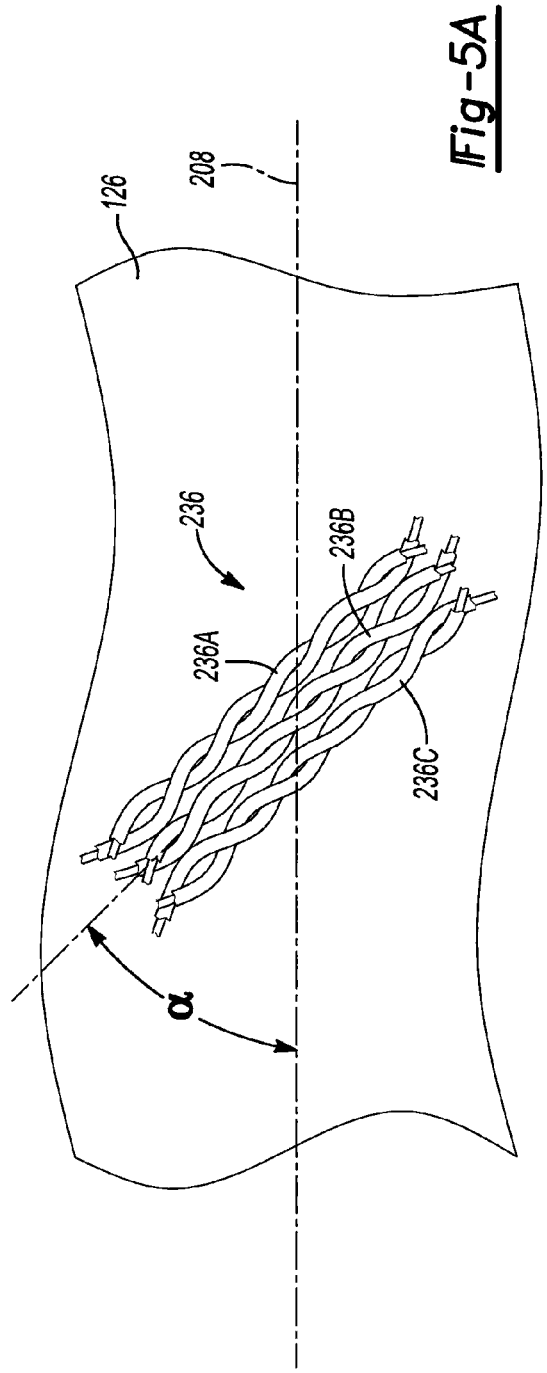

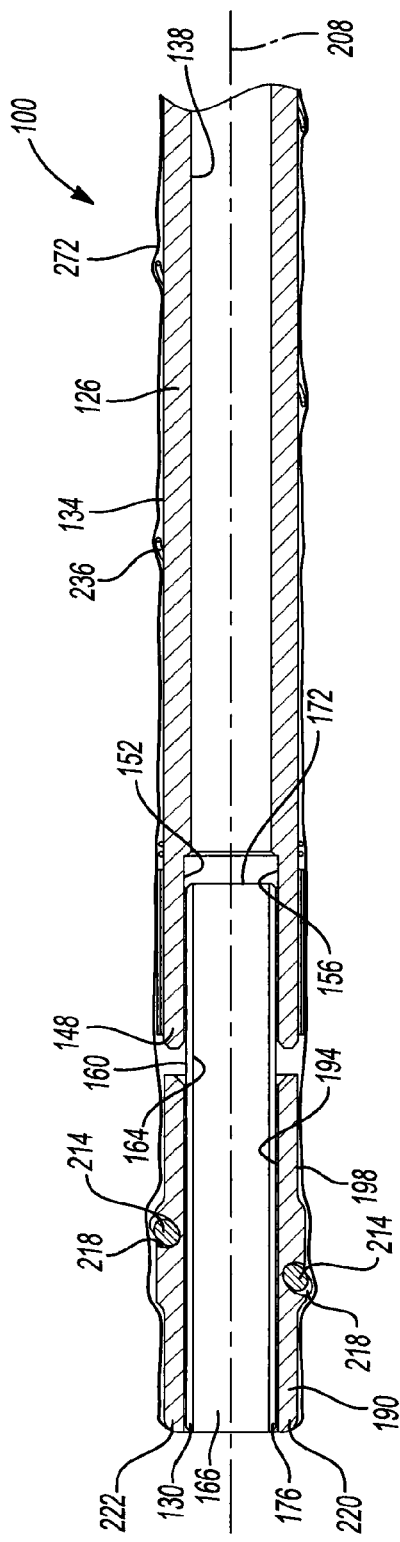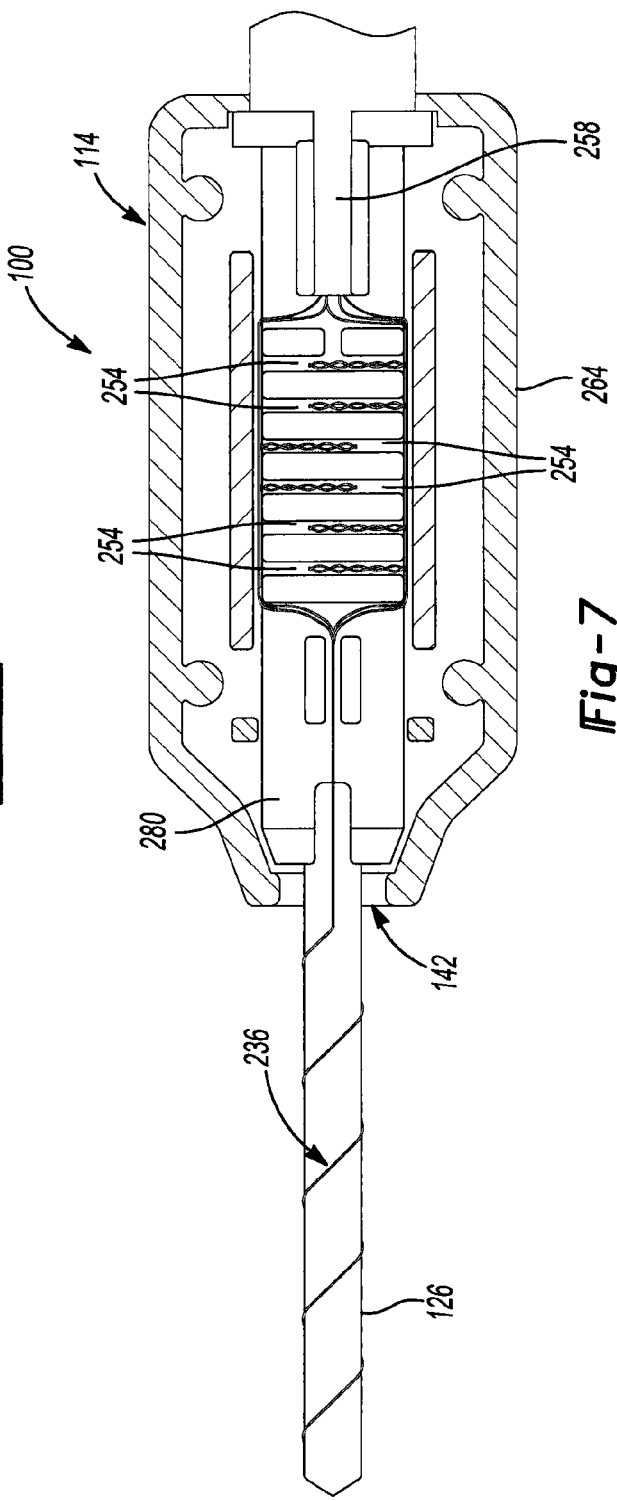

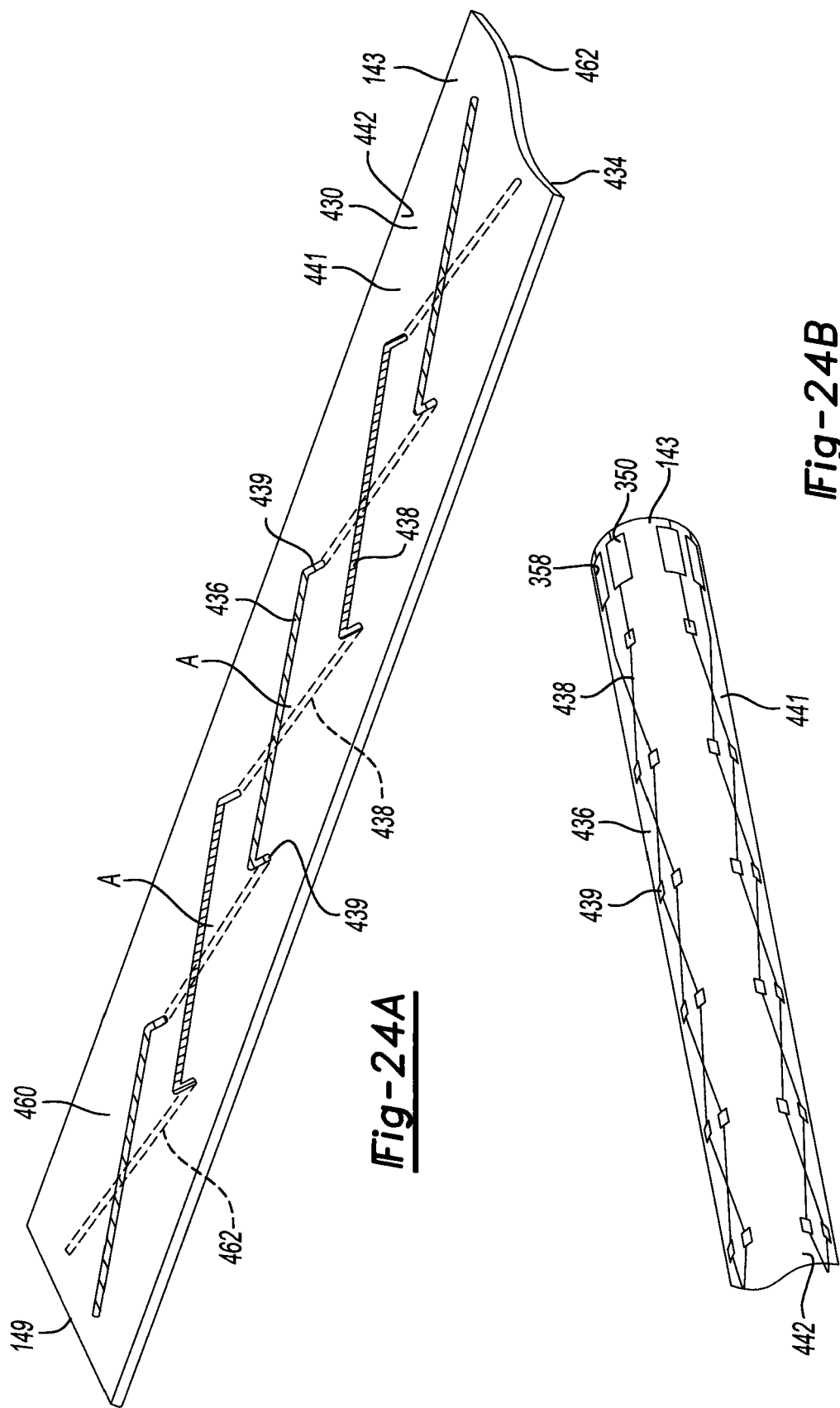

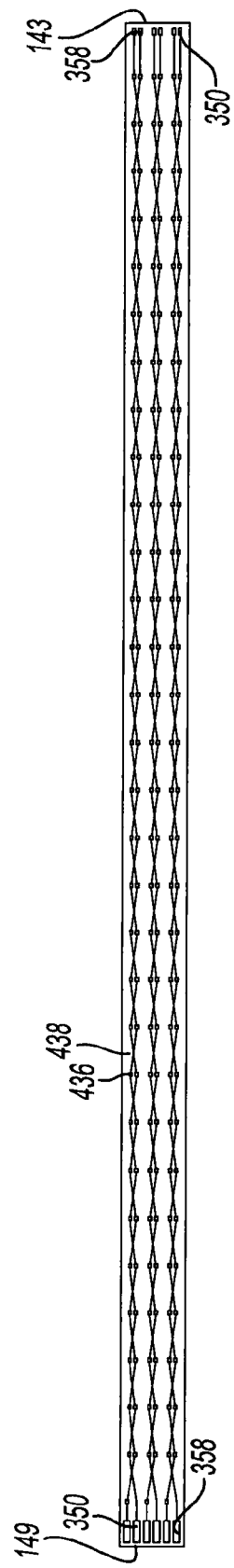
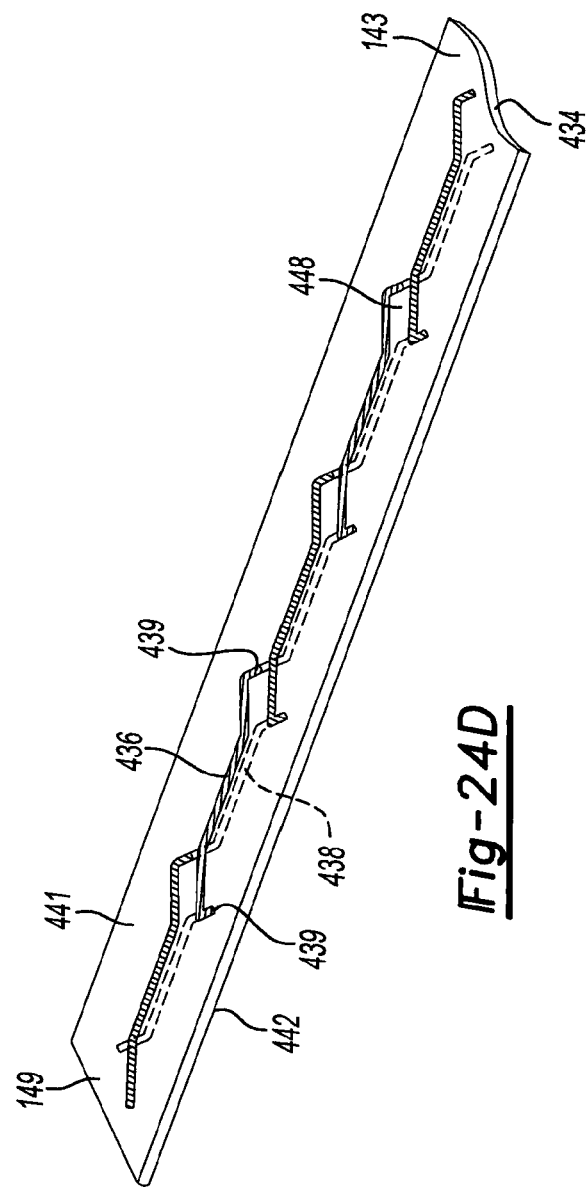
Fig-24C
Fig-24D

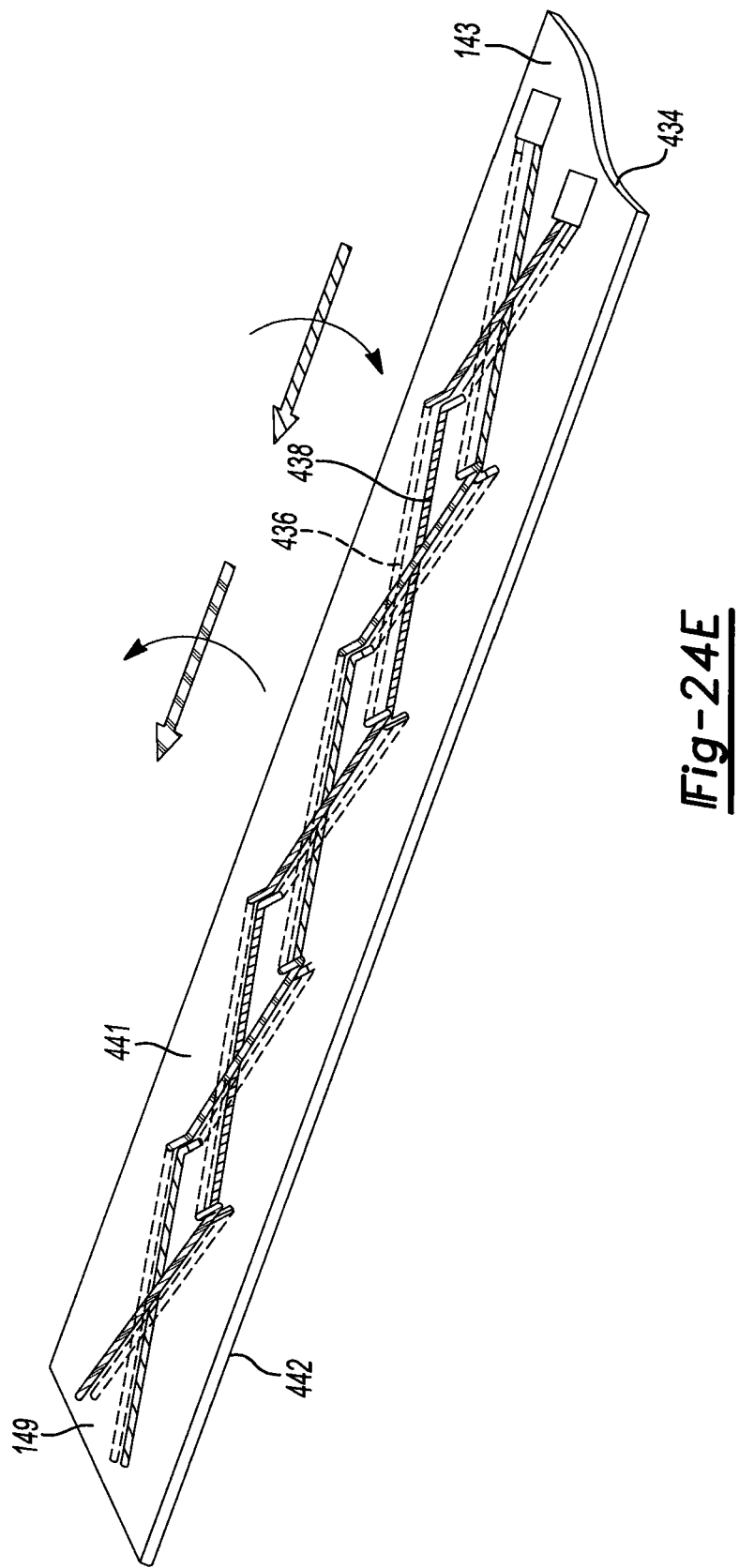

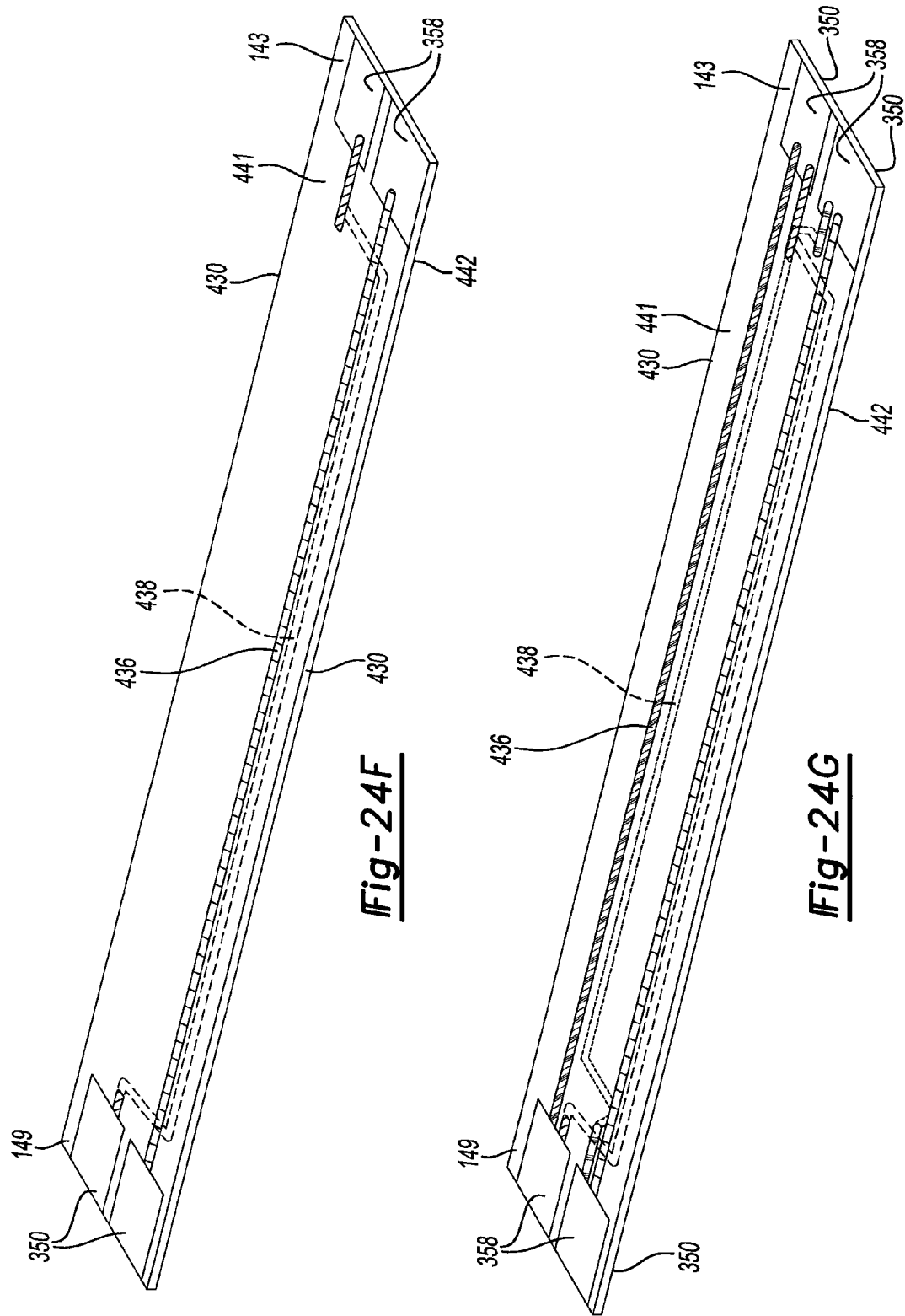

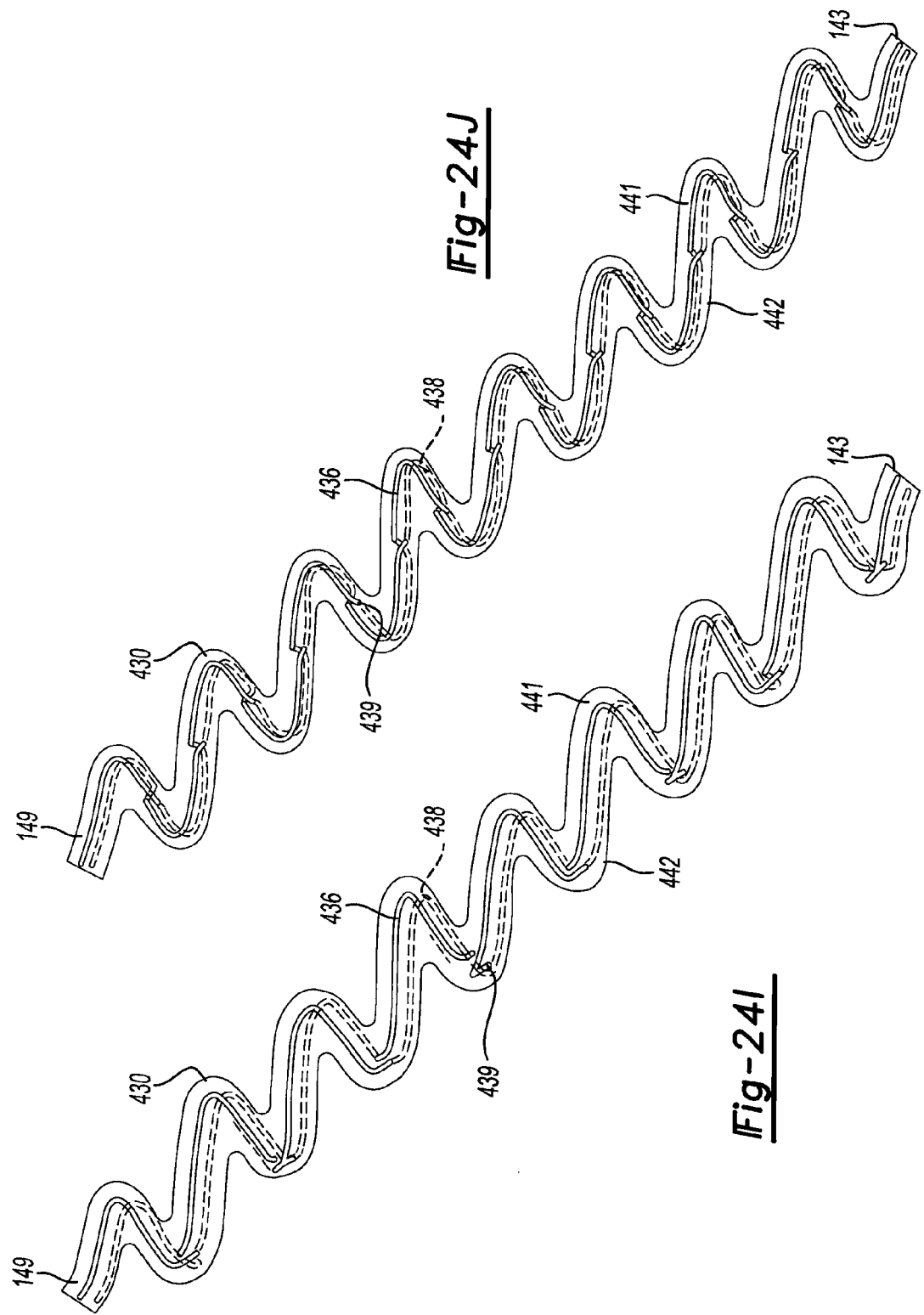

FLEXIBLE CIRCUIT SHEET

CROSS-REFERENCE TO RELATED APPLICATIONS

This application is a continuation-in-part of U.S. application Ser. No. 13/748,150 filed on Jan. 23, 2013, which is continuation-in-part of U.S. application Ser. No. 13/097,243 filed on Apr. 29, 2011, which claims the benefit of U.S. Provisional Patent Application No. 61/330,024 filed on Apr. 30, 2010. This application is also a continuation-in-part of U.S. application Ser. No. 12/400,951 filed on Mar. 10, 2009. The disclosures of the above applications are incorporated herein by reference.

FIELD

The present disclosure relates generally to a flexible circuit sheet and, more particularly, a flexible circuit sheet for a surgical instrument.

BACKGROUND

The statements in this section merely provide background information related to the present disclosure and may not constitute prior art.

Surgical procedures can be performed on anatomies such as the human anatomy for providing a therapy to the anatomy. One area of surgery includes procedures performed on facial cavities of a patient such as on the ear, nose or throat (ENT). In such a procedure, a surgical instrument such as a suction device may be inserted into such a cavity to perform a procedure for example. Because the viewing angle of a surgeon at the area of interest can be obscured by the surrounding tissue of the cavity, the ability of a surgeon to effectively apply a therapy, such as a suction procedure, can be reduced. In some procedures, it may also be difficult to effectively guide the surgical instrument through various shaped cavities of the anatomy. In an effort to address this difficulty, instruments have been developed that include flexible elongated portions configured to be permanently flexible. While these flexible instruments can conform to internal cavities of the anatomy, they do not retain any specific configuration, such that they are generally not suitable for certain procedures, such as an ENT suction procedure.

In navigation systems, instruments are provided with tracking devices. Sometimes, however, such tracking devices can be difficult to manipulate or cumbersome to couple to the instrument, especially instruments with the flexible elongated portions. For example, it can be difficult to electrically couple the tracking devices to associated lead wires relative to the flexible elongated portion. In other instances, the tracking devices can be positioned in a handle or proximal region of the instrument such that if the distal tip moves or is moved relative to the handle, the distal tip can no longer be accurately tracked.

SUMMARY

This section provides a general summary of the disclosure, and is not a comprehensive disclosure of its full scope or all of its features.

A surgical instrument, according to the present teaching has an elongated body portion having a proximal end and a distal end. The body portion has an inner diameter defining a first internal flow passage between the proximal and distal ends, and is formed from a malleable metallic material such that the body portion can be bent between the proximal and distal ends from a first configuration to a second bent configuration and maintain the bent configuration. A handle portion coupled to the proximal end of the body portion and including a second internal passage in fluid communication with the first internal flow passage. A tracking device positioned adjacent the distal end and adapted to cooperate with a navigation system to track the location of a distal tip of the instrument, and including. A flexible circuit is disposed around the body portion from the tracking device to the handle portion, the flexible circuit configured to conform to the bent configuration of the body portion such that they do not strain or break during bending of the body portion.

Further according to the present teachings, a surgical instrument is provided having of an elongated body portion having a proximal end and a distal end. A tracking device is coupled to the elongated tubular body portion adjacent to the distal end. The tracking device is adapted to cooperate with a navigation system and includes a flexible circuit disposed about the tubular body portion between the proximal and distal ends.

Further areas of applicability will become apparent from the description provided herein. It should be understood that the description and specific examples are intended for purposes of illustration only and are not intended to limit the scope of the present teachings.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 2 is a top plan view of an exemplary malleable suction instrument for use with the navigation system according to the principles of the present disclosure;

FIG. 3 is a side view of the exemplary suction instrument according to the principles of the present disclosure;

FIG. 4 is a partial perspective view of a distal region of the exemplary suction instrument having an exemplary flexible circuit sheet according to the principles of the present disclosure;

FIG. 5 is a partial side view of the distal region of the exemplary suction instrument associated with the exemplary flexible circuit sheet according to the principles of the present disclosure;

FIG. 5A is an exploded view of an exemplary wire routing configuration according to the principles of the present disclosure;

FIG. 6 is a partial sectional view of the exemplary suction instrument of FIG. 5 according to the principles of the present disclosure;

FIG. 7 is a partial view of a handle portion of the exemplary suction instrument according to the principles of the present disclosure;

DESCRIPTION OF THE VARIOUS EMBODIMENTS

Figure 1:
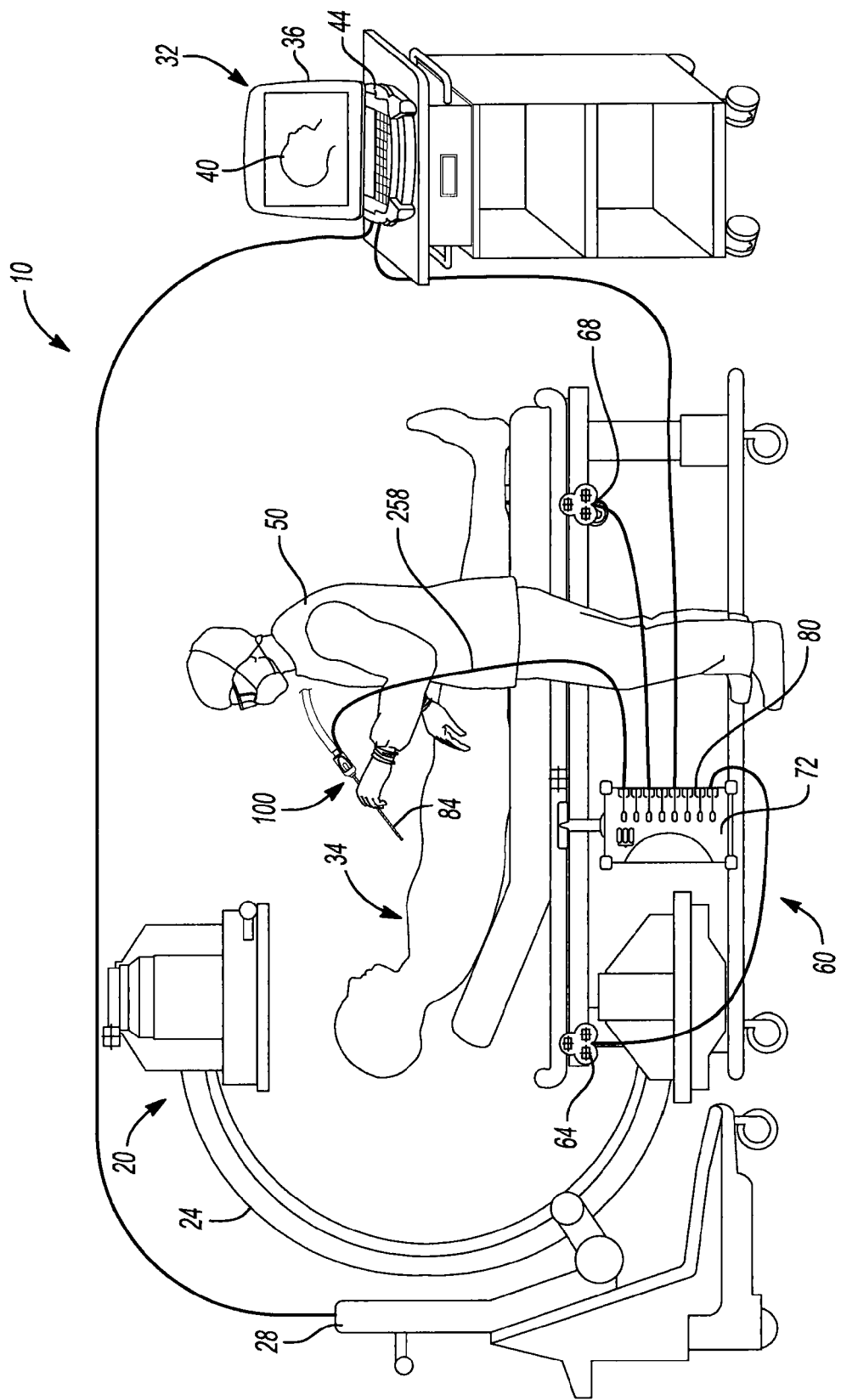
FIG. 1 is a perspective view of an exemplary navigation system according to the principles of the present disclosure.

The following description is merely exemplary in nature and is not intended to limit the present disclosure, its application, or uses. It should be understood that throughout the drawings, corresponding reference numerals indicate like or corresponding parts and features with the various elements in each view being drawn to scale. Although the following description is related generally to a flexible circuit sheet operatively associated with an exemplary flexible or malleable suction instrument, it will be appreciated that the flexible circuit sheet can be associated with various devices and/or instruments, including various other surgical instruments.

Various exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

FIG. 1 is a diagram schematically illustrating an overview of an image-guided navigation system 10 for use in the non-line-of-site navigating of a surgical instrument 100, such as a navigable malleable suction device or suction instrument, according to various exemplary embodiments of the present disclosure. Exemplary navigation systems include those disclosed in U.S. Pat. No. 7,366,562, issued on Apr. 29, 2008 to John H. Dukesherer et al. and U.S. Pat. App. Pub No. 2008/0132909, published Jun. 5, 2008, to Bradley A. Jascob et al., both incorporated herein by reference. Commercial navigation systems include the StealthStation® AxiEM™ Surgical Navigation System sold by Medtronic Navigation, Inc. having a place of business in Louisville, Colo., USA. It should be appreciated that while the navigation system 10 and suction instrument 100 are generally described in connection with an ear, nose and throat (ENT) procedure, navigation system 10 and suction instrument 100 can be used in various other appropriate procedures.

Generally, the navigation system 10 can be used to track a location of an exemplary suction instrument 100, including a distal tip or end thereof, that includes an exemplary flexible printed circuit sheet 232 associated therewith, as will be described herein. Navigation system 10 can generally include an optional imaging system 20, such as a fluoroscopic X-ray imaging device configured as a C-arm 24 and an image device controller 28. The C-arm imaging system 20 can be any appropriate imaging system, such as a digital or CCD camera, which are well understood in the art. Image data obtained can be stored in the C-arm controller 28 and sent to a navigation computer and/or processor controller or work station 32 having a display device 36 to display image data 40 and a user interface 44. The work station 32 can also include or be connected to an image processor, navigation processor, and a memory to hold instruction and data. The work station 32 can include an optimization processor that assists in a navigated procedure. It will also be understood that the image data is not necessarily first retained in the controller 28, but may also be directly transmitted to the workstation 32. Moreover, processing for the navigation system and optimization can all be done with a single or multiple processors all of which may or may not be included in the work station 32.

The work station 32 provides facilities for displaying the image data 40 as an image on the display device 36, saving, digitally manipulating, or printing a hard copy image of the received image data. The user interface 44, which may be a keyboard, mouse, touch pen, touch screen or other suitable device, allows a physician or user 50 to provide inputs to control the imaging device 20, via the C-arm controller 28, or adjust the display settings of the display device 36.

With continuing reference to FIG. 1, the navigation system 10 can further include a tracking system, such as an electromagnetic (EM) tracking system 60. The discussion of the EM tracking system 60 can be understood to relate to any appropriate tracking system. The EM tracking system 60 can include a localizer, such as a coil array 64 and/or second coil array 68, a coil array controller 72, a navigation probe interface 80, and the trackable suction instrument 100. Instrument 100 can include an instrument tracking device or devices 84, as will be discussed herein. Briefly, the tracking device 84 can include an electromagnetic coil to sense a field produced by the localizing coil arrays 64, 68 and provide information to the navigation system 10 to determine a location of the tracking device 84. The navigation system 10 can then determine a position of a distal tip of the suction instrument 100 to allow for navigation relative to the patient 34 and patient space.

The EM tracking system 60 can use the coil arrays 64, 68 to create an electromagnetic field used for navigation. The coil arrays 64, 68 can include a plurality of coils that are each operable to generate distinct electromagnetic fields into the navigation region of the patient 34, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 64, 68 can be controlled or driven by the coil array controller 72. The coil array controller 72 can drive each coil in the coil arrays 64, 68 in a time division multiplex or a frequency division multiplex manner. In this regard, each coil may be driven separately at a distinct time or all of the coils may be driven simultaneously with each being driven by a different frequency.

Upon driving the coils in the coil arrays 64, 68 with the coil array controller 72, electromagnetic fields are generated within the patient 34 in the area where the medical procedure is being performed, which is again sometimes referred to as patient space. The electromagnetic fields generated in the patient space induce currents in the tracking device 84 positioned on or in the suction instrument 100. These induced signals from the tracking device 84 can be delivered to the navigation probe interface 80 and subsequently forwarded to the processor 32. The navigation probe interface 80 can also include amplifiers, filters and buffers to directly interface with the tracking device 84 in the instrument 100. Alternatively, the tracking device 84, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 80.

The tracking system 60, if it is using an electromagnetic tracking assembly, essentially works by positioning the coil arrays 64, 68 adjacent to the patient 32 to generate an electromagnetic field, which can be low energy, and generally referred to as a navigation field. Because every point in the navigation field or patient space is associated with a unique field strength and directions, the electromagnetic tracking system 60 can determine the position of the instrument 100 by measuring the field strength and directions or components thereof at the tracking device 84 location. The coil array controller 72 can receive the induced signals from the tracking device 84 and transmit information regarding a location, where location information can include both x, y, and z position and roll, pitch, and yaw orientation information, of the tracking device 84 associated with the tracked suction instrument 100. Accordingly, six degree of freedom (6 DOF) information can be determined with the navigation system 10.

Referring now to FIGS. 2-10, the navigated malleable surgical instrument 100 will be described in greater detail. In one exemplary configuration, the malleable surgical instrument 100 can be used for suction, including fluid and tissue removal in ENT procedures. It should be appreciated, however, that the navigated malleable surgical instrument 100 can be used in various other surgical procedures as may be desired and can be provided in the form of a malleable or flexible endoscope, a malleable or flexible catheter, and/or a malleable cannula. Thus, while the following description continues with reference to a navigated malleable suction instrument 100, the discussion is also applicable to the surgical instruments discussed above.

Suction instrument 100 can include a tube assembly 110, a handle assembly 114 and a tracking sensor arrangement 118. Suction instrument 100 can be configured for a single use such that it would be disposed after such use. The tube assembly 110 can include a malleable elongated tubular body 126 and an insert portion 130. The tubular body 126 can include an outer diameter 134 and an inner diameter 138 and can have a first end 142 coupled to the handle assembly 114 and a second opposite end 148 configured to receive insert portion 130, as shown in FIG. 6. The second end 148 can include an internal annular recess 152 having an inner diameter 156 greater than the inner diameter 138 of the remaining portion of body 126, as also shown in FIG. 6. The malleable elongated body 126 can be formed from various aluminum alloys, such as AL 3003-O, various stainless steel alloys, such as 304 annealed, as well as various other materials including titanium, niobium, molybdenum, tantalum, nitinol, vinyl, and multi-lumen materials, such that it is malleable to facilitate being bent or formed into various configurations and retaining the bent or formed configuration, as will be discussed herein. The body 126 can also be provided in various lengths and diameters, including 7, 9 and 12 French diameters.

The insert portion 130 can be configured to provide non-malleable support for at least the tracking sensor 84. Insert portion 130 can include an outer diameter 160 substantially equal to the inner diameter 156 of annular recess 152, and an inner diameter 164 substantially equal to the inner diameter 138 of malleable elongated body 126, as also shown in FIG. 6. In this manner, the substantially equal inner diameters 138, 164 can provide for a substantially constant flow path 166 for suction. It should be appreciated, however, that the inner diameters 138, 164 can also be provided with varying dimensions. The insert portion 130 can also include an exemplary axial length of 10 to 15 mm, including 14 mm. Insert portion 130 can include a first end 172 and a second opposite end 176. The first end 172 of the insert portion 130 can be received in annular recess 152, as shown in FIG. 6. Insert portion can include a rigid construction to facilitate receiving and housing tracking device 84, as will be described herein. In this manner, insert portion 130 can be formed or manufactured from stainless steel or other biocompatible rigid materials such that insert portion 130 is not malleable like elongated body 126. The insert portion can also include an exemplary axial length of approximately 10 mm.

Insert portion 130 can include a sleeve 190 received on an exterior thereof, as shown in FIGS. 5 and 6. Sleeve 190 can include an inner diameter 194 substantially equal to the outer diameter of insert portion 130, and an outer diameter 198 substantially equal to the outer diameter 134 of body 126. It should be appreciated that sleeve 190 can also be configured with different diameters relative to body 126. Sleeve 190 can extend over a portion of insert 130 from the first end 172 of the insert portion 130 towards the second end, as shown in FIG. 6. In one exemplary configuration, sleeve 190 can extend from the first end 172 and contact the first end 142 of body 126 when the insert portion 130 is coupled to annular recess 152 of body 126. In another exemplary configuration, sleeve 190 can extend from the first end 172 of body portion 130 in a similar manner as discussed above, but can stop short of the first end 142 of body 126, as shown in FIG. 6. Sleeve 190 can be fixed to insert portion 130, and insert portion 130 can be fixed to annular recess 152 with an appropriate adhesive. Sleeve 190 can be formed of a polymeric material or other suitable materials. Sleeve 190 can also include a first end 220 configured to substantially align with the second end 176 of insert 130. The first end 220 can include a rounded or chamfered blunt distal tip or end part 222 such that it can be placed against surrounding tissue during a suction procedure without cutting or damaging such tissue. In one exemplary configuration, end part 222 can extend over insert portion 130 so as to prevent cutting or damaging tissue.

With particular reference to FIGS. 4 and 5, sleeve 190 can include a plurality of flattened sections 206 configured to facilitate receiving and supporting the tracking sensor arrangement 118, as will be described herein. In one exemplary configuration, sleeve 190 can include at least three flattened sections 206 configured to attachably receive tracking device 84. In this configuration, the tracking device 84 can include three coil assemblies 214, as will be described herein. Briefly, in one exemplary configuration, the three coil assemblies 214 can each include a cylindrical configuration as shown in FIGS. 4 and 5, having an overall axial length of approximately 1.5 mm to 2.7 mm, an overall diameter of approximately 0.3 to 0.6 mm, and a plurality of wire windings wound along a cylindrical base to form the cylindrical configuration. The plurality of windings can form the coil assembly 214 having the generally uniform cylindrical configuration, as generally shown in FIG. 5. Each flattened section 206 can include a slot or depression 218 formed therein and configured to receive a corresponding coil assembly 214, as shown for example in FIGS. 5 and 6. Each slot 218 can be formed in the corresponding flattened section 206 at a 35 to 75 degree angle, including a 55 degree angle, to a longitudinal axis 208 of the tube assembly 110. In one exemplary configuration, each slot 218 can be formed at a 55 degree angle to longitudinal axis 208, as shown in FIG. 5. Each of the three flattened sections 206 can be positioned equidistantly or 120 degrees around a circumference of sleeve 190 so that the three coil assemblies 214 are therefore likewise positioned equidistantly around the circumference of sleeve 90, as also generally shown in FIGS. 4-6. It should be appreciated that the coil assemblies can also be coupled to the sleeve without the flattened sections 206, and can be aligned at different orientations relative to the longitudinal axis, including parallel thereto. In this regard, the sleeve 190 can include an outer surface with a circular shape in cross-section configured to receive the coil assemblies 214.

The coil assemblies 214 can include three coil assemblies as described above that cooperate with the navigation system 10 such that 6 DOF tracking information can be determined. It should be appreciated, however, that two coil assemblies 214 could also be used in conjunction with navigation system 10 such that 6 DOF tracking information can also be determined. In a configuration where three coil assemblies 214 are utilized, two of the three coil assemblies can be positioned at an angle relative to the longitudinal axis 208 with the third coil assembly being positioned at an angle relative to the longitudinal axis 208 or parallel thereto. The three coil assemblies 214 can also each be positioned at an angle relative to each other. As discussed above, an exemplary angle of the three coil assemblies 214 relative to the longitudinal axis 208 can be 55 degrees, which also provides for optimal packaging and spacing of the coil assemblies circumferentially around sleeve 190. It should be appreciated that while an angle of 55 degrees has been discussed, other angles could be utilized with coil assemblies 214 and instrument 100 as may be required. It should also be appreciated, as discussed above, that the coil assemblies could be positioned parallel or perpendicular to the longitudinal axis 208.

In a configuration where tracking device 84 includes two coil assemblies 214, the two coil assemblies can similarly be positioned equidistant or 180 degrees spaced around an outer perimeter of sleeve 190, as well as can each be positioned at an angle relative to each other and at an angle relative to the longitudinal axis 208 of the tube assembly 110. In this configuration, the two coil assemblies can also cooperate with navigation system 10 such that 6 DOF tracking information can be determined. In one exemplary configuration, the two coil assemblies 214 can be positioned at an angle of about 35 to 75 degrees, including about 55 degrees relative to longitudinal axis 208 of the tube assembly 210.

Figure 8:
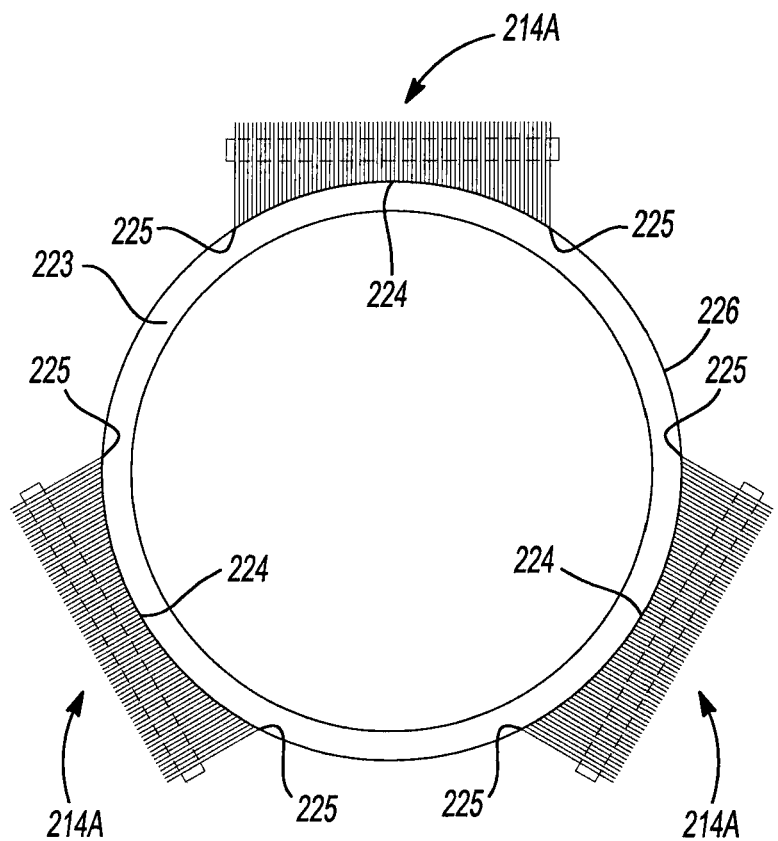
FIGS. 8 and 9 illustrate views of exemplary alternative tracking sensor configurations according to the principles of the present disclosure.
Figure 9:
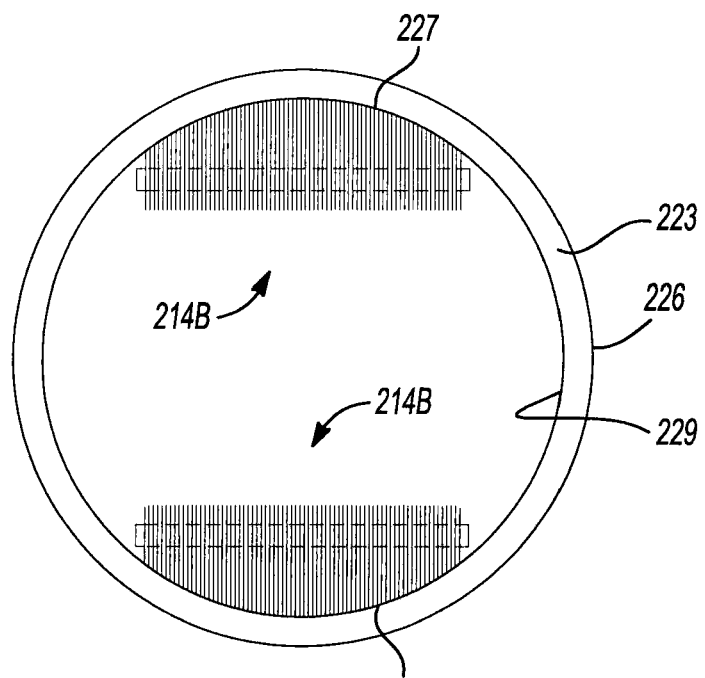

With additional reference to FIGS. 8 and 9, two exemplary coil assemblies 214A and 214B having alternative winding configurations are illustrated operatively associated with an exemplary tubular structure 223 of an exemplary instrument. Coil assemblies 214A and 214B can each include an overall non-linear shape as compared to the overall cylindrical configuration of coils assemblies 214 shown in FIG. 5. Coil assembly 214A can include a central arcuate depression or concavity 224 such that the depression 224 has a smaller outer diameter than opposed ends 225 of the plurality of windings, as generally shown in FIG. 8. The winding configuration of coil assembly 214A can provide an ability to maximize an amount of coil windings on a base wire while working towards minimizing an overall outer dimension or size of an instrument. In this regard, coil assembly 214A is shown in FIG. 8 with the arcuate depression 224 substantially conforming to an outer surface 226 of the tubular structure 223 such that the coil assembly or assemblies 214A essentially nest around the outer surface 226 of the tubular structure. In this regard, because of the general clearance provided by a cylindrical coil assembly positioned adjacent to an outer diameter of the tubular structure 223, a gap or space 221 on either end of the coil can include additional windings without effectively increasing the overall outer diameter of the entire assembly. This can allow for greater or stronger sensitivity in the navigated space.

With particular reference to FIG. 9, coil assembly 214B can include an overall arcuate convex shape 227 configured to conform to and nest within an inner diameter 229 of the exemplary tubular structure. Similar to coil assembly 214A, such a configuration can provide for maximizing an amount of windings on the base wire while also working towards minimizing the inner diameter 229 of the tubular structure 223 that would be required to receive one or more coil assemblies 214B.

With particular reference to FIGS. 5 and 5A, the tracking sensor arrangement 118 will now be described in detail. Tracking sensor arrangement 118 can include the tracking device 84 having the two or three coil assemblies 214, as well as a first set of lead wires 228, the flexible printed circuit board or sheet 232 and a second set of lead wires 236. The first set of lead wires 228 can include a pair of lead wires 228A and 228B for each coil assembly 214, as generally shown in FIG. 5. Each respective pair of lead wires 228A and 228B can be routed to a first end of a respective pair of circuit connections 240 on flexible printed circuit sheet 232. As will be discussed in greater detail below, the flexible circuit sheet 232 can facilitate improving the time and cost associating with terminating fine wires utilized in medical and other instruments while also providing the flexibility necessitated for such instruments. It should be appreciated that while tracking device 84 is described as having three coil assemblies, more or less coil assemblies can be utilized as may be desired or required depending on, for example, characteristics of the navigation system being utilized as well as the number of degrees of freedom desired.

The flexible printed circuit sheet 232 can include a flexible backing or base layer 244 such that it can readily conform to the contour of an outer surface of the body 126, as shown for example in FIG. 4. The flexible printed circuit sheet 232 can wrap entirely or partially around a perimeter of the body 126 and can be positioned adjacent the second end 148 of body 126, as generally shown in FIGS. 5 and 6. In this manner, the insert portion 130, in its inserted position shown in FIG. 6, can be under all or substantially all of the flexible printed circuit sheet 232. The rigid insert portion 130 can thus prevent the malleable body 126 from bending or flexing in a region of the flexible printed circuit sheet 232. In one exemplary configuration, the flexible printed circuit sheet 232 can be an integral part of sleeve 190. In another exemplary configuration, flexible printed circuit sheet 232 can be positioned in a similar manner on sleeve 190. In this configuration, flexible printed circuit sheet 232 can be positioned on sleeve 190 between coil assemblies 214 and the end of sleeve 190 adjacent the second end 148 of body 126.

The second set of lead wires can include three respective pairs of wires 236A, 236B, 236C, as generally shown in FIG. 5 with reference to the partial exploded view in FIG. 5A. It should be appreciated that while FIGS. 2-5, 6-7 and 10 show the second set of lead wires 236 as one element, this is for illustration purposes only and it should be understood that the second set of lead wires shown in FIGS. 2-5, 6-7 and 10 include the three respective pairs of lead wires 236A-C, as shown in FIG. 5A. Each pair of lead wires 236A-C can be twisted together and positioned adjacent each other, as also shown in FIG. 5A. The twisted pairs 236A-C of wires can reduce electrical interference or cross-talk between each pair of adjacent lead wires as well as minimize pickup from an associated electromagnetic navigation system. Each pair of lead wires can be connected to a single coil assembly 214 via the flexible printed circuit sheet 232. The lead wires can also include a Teflon coating or other appropriate lubricous or friction reducing coating on an outer surface thereof. Each pair of lead wires 236A-C can be coupled to an opposite end of respective circuit pads 240 on the flexible printed circuit sheet 232. It should be appreciated that the lead wires 228 could alternatively extend up the body 126 as a twisted pair of lead wires without the use of the flexible printed circuit sheet 232, or could extend up to and be terminated directly to the respective twisted pair of lead wires 236.

The second set of lead wires 236, which includes the three pairs of twisted wires 236A-C, can be helically wound around elongated body 126 from the flexible printed circuit sheet 232 to the second end 148, as generally shown for example in FIGS. 3-5A. The wires 236 can be wound around the outside of body 126 at an angle α relative to the longitudinal axis 208 of approximately 0 to 85 degrees, including about 30 degrees, as generally shown in FIGS. 5 and 5A. Each revolution of the wires 236 around body 126 can be spaced apart from each other by a distance D of approximately 2 to 45 mm, including about 5 mm, as shown with reference to FIG. 5. In one exemplary configuration, the range can include from about 15-45 mm. The helical winding of the wires 236 at an acute angle relative to the longitudinal axis along with the relatively close spacing of the wires and the Teflon coating facilitate being able to bend the malleable body 126 at significant angles, including beyond ninety degrees, without breaking or otherwise damaging the wires 236, as will be discussed herein. It should be appreciated that the wires 236 can also be positioned along body 126 in a single revolution from the flexible printed circuit sheet 232 or the tracking device 84 to the second end 148. In this regard, the revolution spacing can be from about 2 mm to a length of the body 126. The wires 236 can also be positioned along body 126 from the flexible printed circuit sheet 232 to the second end 148 without being wound around body 126.

Once the second set of wires 236 has been helically wound around the outside of tubular body 126 to the first end 142, the wires can be routed into slots 254 in handle assembly 114 and connected to respective lead wires of a cable connector assembly 258, as generally shown in FIG. 7. The cable connector assembly 258 can be connected to the navigation probe interface 80, as generally shown in FIG. 1. The handle assemble 114 can include two half sections 264, with one half section being shown in FIG. 7 for illustration purposes.

With particular reference to FIG. 6 and continued reference to FIGS. 2-5A, 7 and 10, the tube assembly 110 can include a polymeric outer heat shrink 272 covering the entire assembly, as shown in the cross-sectional view of FIG. 6. Thus, the heat shrink 272 can cover the elongated body 126, the insert portion 130, and the sensor arrangement 118 including the wires helically wound along the body 126. The heat shrink 272 can provide an outer covering or shell over the tube assembly 110 and sensor arrangement 118 while providing sufficient flexibility for both bending of the body 126 and slight relative movement of the helically wound wires 236 as a result of the bending. In this regard, the wires can be moveably captured between the heat shrink and the tubular body. The heat shrink covering can also serve as an electric isolation barrier. It should be appreciated that while the heat shrink covering is only shown in FIG. 6, it has not been shown in the other various views for clarification purposes only to better illustrate the sensor arrangement 118 and routing of wires 236. In this regard, it should be understood that the heat shrink 272 can cover the tube assembly 110 and sensor arrangement 118 shown in FIGS. 2-10.

As discussed above, the handle assembly 114 can include multiple components, such as for example two halves, with one of the halves shown in FIG. 7 receiving the first end of the suction tube assembly 110 in fluid communication with a suction passage 280 formed therein. The suction passage 280 can terminate at a connector 284 protruding from a proximal end of the handle (FIGS. 2 and 3) and can be configured to receive a suction hose or other arrangement in fluid communication with a suction source (not shown). Once the wires are connected to the cable assembly and routed in the slots 254 as discussed above, the other half of handle assembly 114 can connected and an adhesive can be used to bond the handle halves together to form the handle as shown in FIGS. 2 and 3.

With particular reference to FIG. 2, handle assembly 114 can include a suction adjustment feature 290 which can be in the form of a bore 292 extending from an outer surface 294 of the handle assembly 114 and into fluid communication with the suction passage 280. In operation, a surgeon or user 50 of the instrument 100 can place their thumb or another object over the bore 292 to vary an opening of the bore 292 and thus vary an amount of suction pressure realized in the flow path or passage 166. For example, if the bore 292 is left completely open or uncovered, a majority if not all of the suction will be through the bore 292 and not the first end 172 of insert portion 130. On the other hand, if the bore 192 is completely covered or closed off, a maximum amount of suction will be realized at end 172. Varying the opening of bore 292 between fully closed and fully opened can therefore correspondingly vary an amount of realized suction at end 172.

Figure 10:
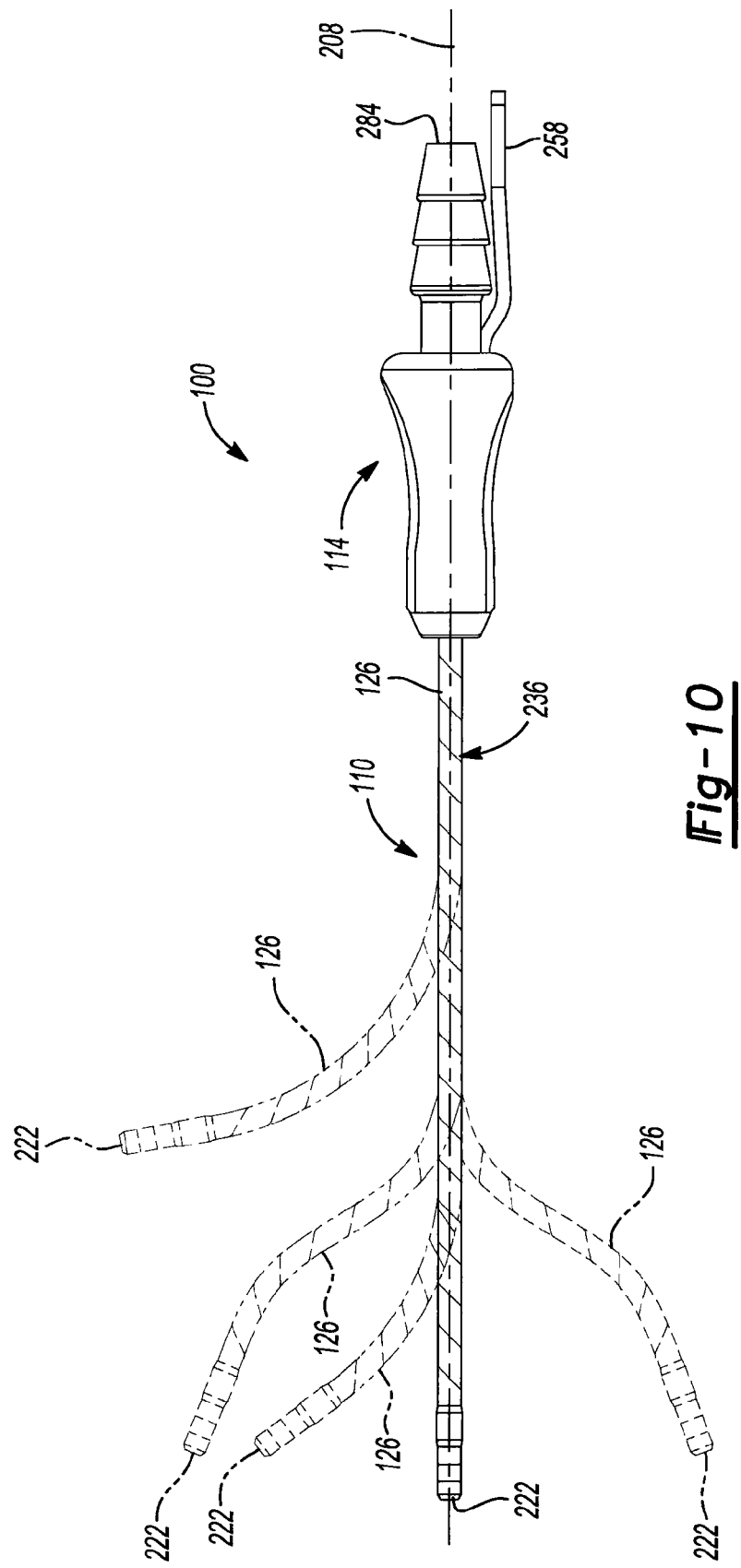
FIG. 10 is a view of exemplary bent or formed configurations of the exemplary malleable suction instrument according to the principles of the present disclosure.

In operation and with additional reference to FIG. 10, the malleable elongated body 126 can be bent into various configurations, as generally shown by the exemplary configurations 300A-D. The malleable nature of body 126 can provide the ability for body 126 to be bent into such various configurations without kinking and can maintain the various configurations until bent or shaped into another configuration. Further, malleable body 126 can be bent or shaped as discussed above without require additional tools, such as a mandrel to facilitate the bending. This is advantageous, for example, in that a surgeon can bend body 126 multiple times by hand during a procedure in close proximity to the patient without having to resort to additional tools or other equipment to facilitate the bending while performing the procedure.

Moreover, the helically wound configuration of wires 236 along with the Teflon coating provides for the ability to bend malleable body 126 at various angles including through ninety degrees without breaking the wires. More specifically, by winding wires 236 helically around body 126 at an angle relative to the longitudinal axis and at a close proximity to each other, the wound wires can conform to the bent shape and move or flex axially with the bent tube such that they do not strain and/or break during the bending. In addition, the Teflon coating provides added lubricity for the wires to have relative motion between the tube and the outer shrink coating 272 during bending.

Further, by providing the tracking device 84 near the distal tip 222, the distal tip 222 of the suction instrument can be tracked to provide substantially accurate position data for the distal tip of suction instrument 100 when out of a line of sight in a body cavity of patient 34. This is particularly useful for the malleable suction instrument 100 because, for example, the tip can be bent or moved relative to the handle and still be tracked. On the other hand, if the tracking device was in the handle (such as in a hind tracked system) and the body 126 was subsequently bent or shaped, the navigation system would no longer be able to accurately track the position of the distal tip. In this regard, the present teaching provide a tip tracked malleable suction instrument that can be bent or shaped into various configurations as may be required during a procedure, and the distal tip can be accurately tracked in any of the various bent positions.

In use, the patient 34 can be positioned on an operating table or other appropriate structure and appropriate image data of a patient or navigation space can be obtained, such as an ENT area. The image data can be registered to the navigation space as is known in the art. The surgeon 50 can determine a shape of the malleable suction instrument 100 to reach a target site and bend the suction instrument 100 to the determined shape where instrument 100 retains the bent shape, as discussed above. The bent or shaped surgical instrument 100 can then be guided to the target site with crosshairs representing the position of the distal tip of instrument 100 being superimposed on the image data. The crosshairs can show the tracked relative position of the distal tip as instrument 100 is navigated to the target site. In addition, if during navigation of the shaped instrument 100 to the target site, the surgeon determines that the shaped configuration will need to be altered, the surgeon can bend and/or reshape the instrument 100 to a newly shaped configuration and proceed again as discussed above.

Figure 11:
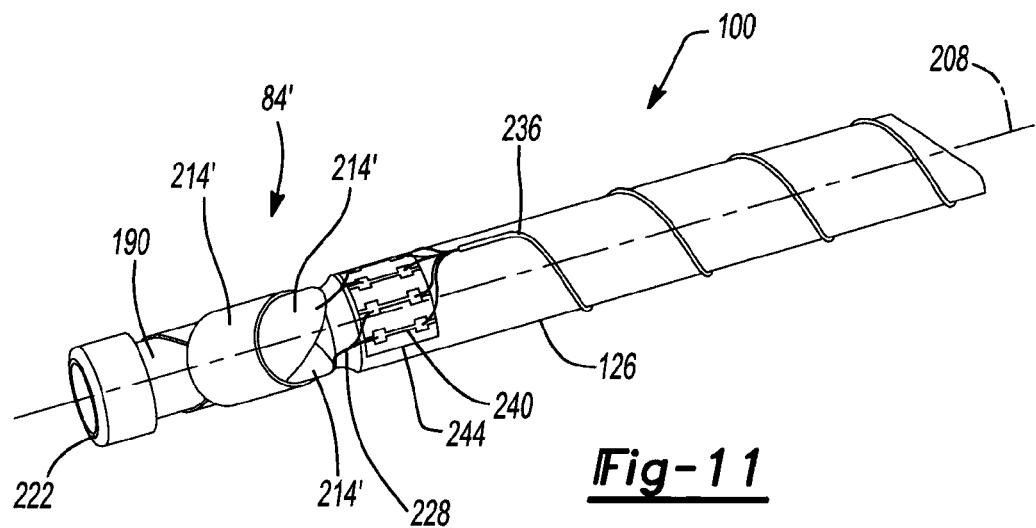
FIG. 11 is a partial perspective view of the distal region of the exemplary suction instrument illustrating an exemplary alternative tracking arrangement associated with the exemplary flexible circuit sheet according to the principles of the present disclosure.

With additional reference to FIG. 11, an alternative tracking device arrangement 84' will now be discussed. As can be seen in FIG. 11, tracking device 84' can include two or three wrapped coil assemblies 214' that can be used in place of the coil assemblies 214. Coil assemblies 214' can be wrapped around sleeve 190 proximate the distal tip 222. In one exemplary configuration, the coil assemblies 214' can be individually wrapped around sleeve 190 in an overlapping manner with a wrap axis having a non-normal and non-parallel angle to longitudinal axis 208. In the exemplary configuration illustrated, coil assemblies 214' can be wrapped around sleeve 190 at an angle relative to each other and longitudinal axis 208. In another exemplary configuration, coil assemblies 214' can be wrapped around sleeve 190 and spaced axially apart from each other. A further discussion of the coil assemblies 214' can be found in U.S. application Ser. No. 12/770,181, filed on Apr. 29, 2010 and entitled "Method and Apparatus for Surgical Navigation", the disclosure of which is incorporated by reference herein in its entirety.

Figure 12:
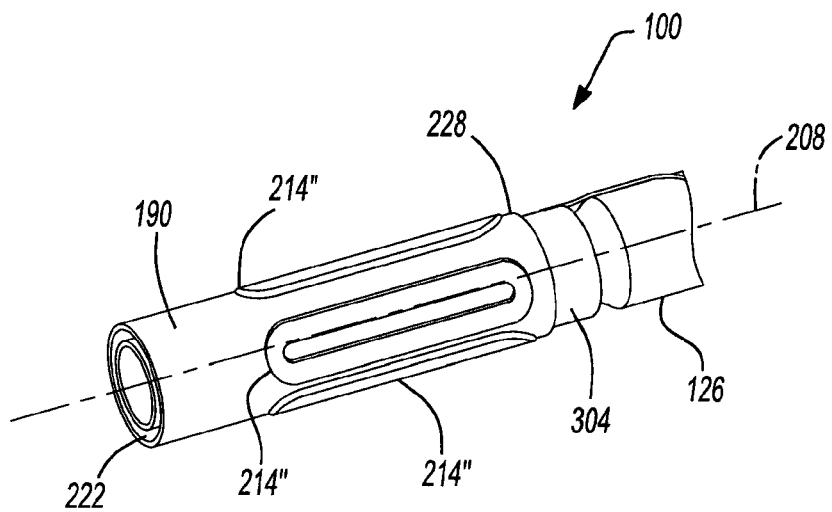
FIG. 12 is a partial perspective view of the distal region of the exemplary suction instrument illustrating another exemplary alternative tracking arrangement according to the principles of the present disclosure.

With additional reference to FIG. 12, another alternative tracking device arrangement 84" is shown associated with instrument 100. Tracking device 84" can also be used in place of tracking device 84 and can include a plurality of oval coil assemblies 214" positioned about sleeve 190 proximate distal tip 222. In one exemplary configuration, two to four coil assemblies 214" can be positioned about sleeve 190 proximate distal tip 222. In the exemplary configuration illustrated, four coil assemblies 214" can be circumferentially spaced around sleeve 190 proximate distal tip 222, and an axial coil 304 can be positioned proximally of coil assemblies 214", as shown in FIG. 12. In one exemplary configuration, two oval coil assemblies 214" can be provided with the axial coil 304. The two coil assemblies 214" can also include two pair of coil assemblies 214" provided with the axial coil 304.

The coil assemblies 214" can be formed in various selected shapes, such as elliptical, circular, or oval. In one exemplary configuration, the axial coil 304 can be concentric with and wrapped around an outer surface of sleeve 190 or body 126, as shown in FIG. 12. A further discussion of coil assemblies 214" and axial coil 304 can be found in U.S. application Ser. No. 13/016,740, filed on Jan. 28, 2011 and entitled "Method and Apparatus for Image-Based Navgation", the disclosure of which is incorporated by reference herein in its entirety.

Figure 13A:
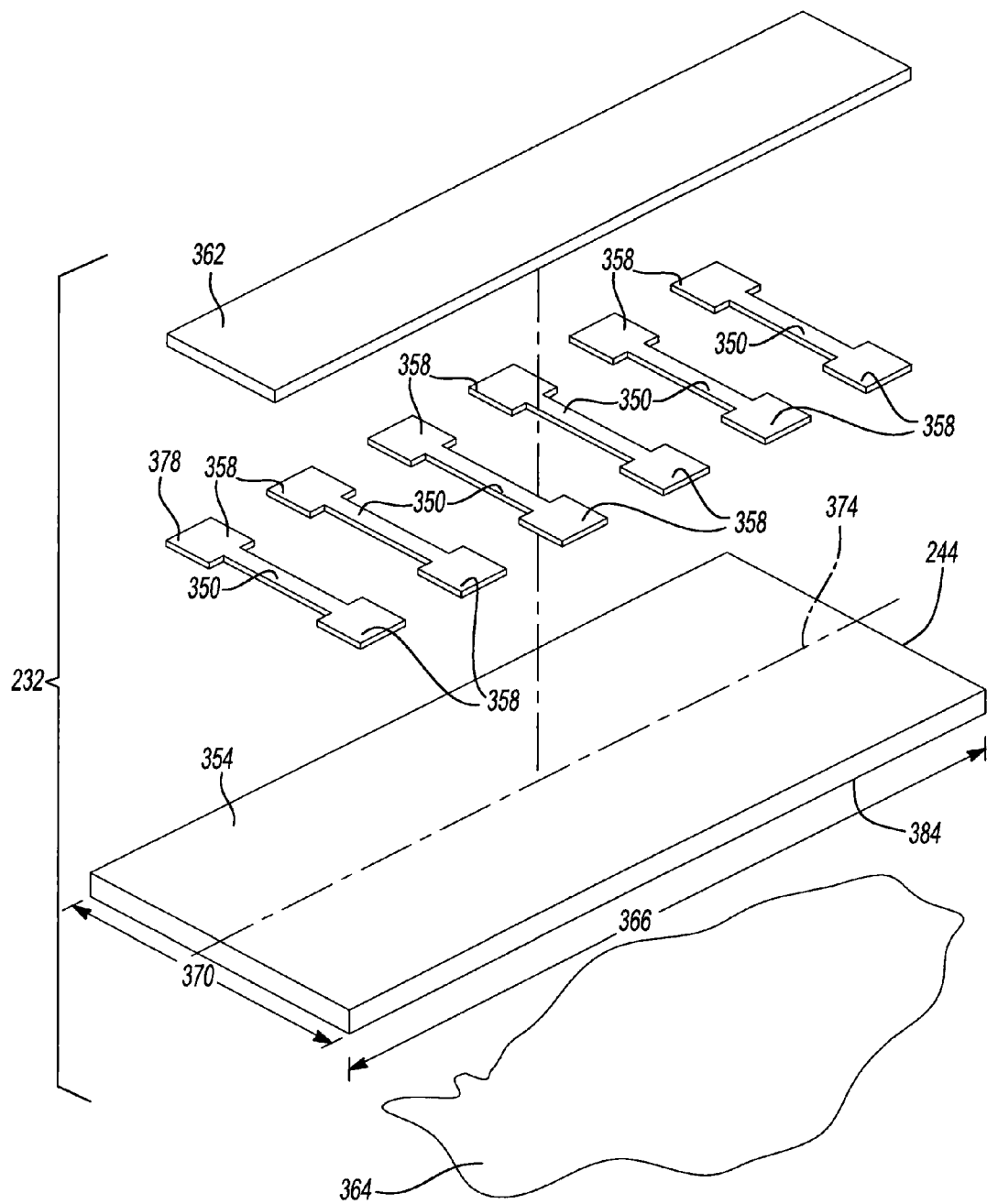
FIG. 13A is an exploded perspective view of an exemplary configuration of the flexible printed circuit sheet according to the principles of the present disclosure.

Turning now to FIGS. 13A-18, the flexible printed circuit sheet 232, including various exemplary configurations thereof, will now be discussed in greater detail. With particular reference to FIGS. 13A-13B, one exemplary configuration of the flexible printed circuit sheet 232 is shown in both an exploded view (FIG. 13A) and an assembled view (FIG. 13B). Flexible printed circuit sheet 232 can include the flexible backing or base layer 244, one or more circuit or conductive traces, such as copper traces 350, positioned on a first or upper side 354 of base layer 244, coupling pads 358 associated with traces 350, and an insulative layer 362 formed over at least the copper traces 350 and coupled to base layer 244. It will be appreciated that while copper traces 350 are shown positioned on upper side 354, the copper traces 350 can also be positioned on an opposite lower side of base layer 244. While the discussion will continue with reference to the conductive traces being copper traces 350, the conductive traces can also be formed from metal, nickel, gold, or copper with nickel/gold plating.

The flexible printed circuit sheet 232 can provide a mechanism for facilitating fine gauge wire termination of associated sensors or coils and lead wires, such as wires 228 and 236 of exemplary suction instrument 100. The flexible printed circuit sheet 232 can also enable manufacturing and design flexibility in connection with use of circuit sheet 232 on instruments and other devices that are flexible and/or conformable. For example, conventional techniques for electrically terminating sensor wires to lead wires can include directly connecting the sensor wires to the lead wires via soldering. As can be appreciated, such a technique is very time and labor intensive considering that the sensor and lead wires can include 58 AWG wire with an outer diameter of approximately 0.01 mm. Indeed, such conventional techniques for soldering the sensor wires to the lead wires often require performing the process under a microscope or other magnifying apparatus, which can further drive cost and expense into the manufacturing process.

As will also be discussed in greater detail below, the exemplary flexible circuit sheets discussed herein can provide for improved efficiency and cost reduction in terminating such fine gauge sensor and lead wires, especially for medical instruments having size or volume constraints and that also require flexibility or conformability. In this regard, the coupling 358 on the flexible circuit sheet 232 can be orders of magnitude bigger than the outer diameter of the wires to be terminated, such as a 0.1 mm to 0.5 mm square pad, for example. In an exemplary configuration, the coupling pads 358 can have a large surface area for the wires to be terminated such that, for example, a primary linear dimension of the coupling pads 358 can be orders of magnitude bigger than the outer diameter of the wires to be terminated. In one exemplary configuration, the wires to be terminated can include an outer diameter of between approximately 0.03 mm to 0.05 mm. In an exemplary configuration, the wires to be terminated can include 58 AWG wire having an outer diameter of approximately 0.01 mm. This can, among other things, facilitate easier and more efficient termination of the fine gauge wire due to the larger size of coupling pads 358.

The base layer 244 can be formed form various materials having appropriate insulative properties and appropriate material properties such that base layer 244 is flexible and can conform to various surface geometries. For example, the base layer 244 (as well as the assembled printed circuit sheet 232) can conform to the outer tubular surface of the malleable suction instrument 100. In one exemplary configuration, the flexible nature of flexible circuit sheet 232 can facilitate movement with tube assembly 110 of malleable instrument 100 (e.g., FIG. 10) once adhered thereto. In one exemplary configuration, the base layer 244 can be formed from a polymeric material, including but not limited to, a polyimide. In the exemplary configuration illustrated in FIGS. 13A-13B, the base layer 244 can include a length 366 of approximately 7 mm and a width 370 of approximately 3 mm. It should be appreciated, however, that the size and shape of base layer 244 can vary depending on a particular application.

The copper traces 350 can be positioned or printed in any desired orientation on base layer 244, including substantially perpendicular to a longitudinal axis 374 of base layer 244. The copper traces 350 can similarly include varying lengths and widths depending on the particular configuration of flexible printed circuit sheet 232. In the exemplary configuration illustrated in FIGS. 13A-13B, the copper traces 350 can include a length of approximately 1.25-3.0 mm and a width of approximately 0.15 mm. The copper traces 350 can include a thickness of approximately 0.01-0.04 mm.

Figure 13B:
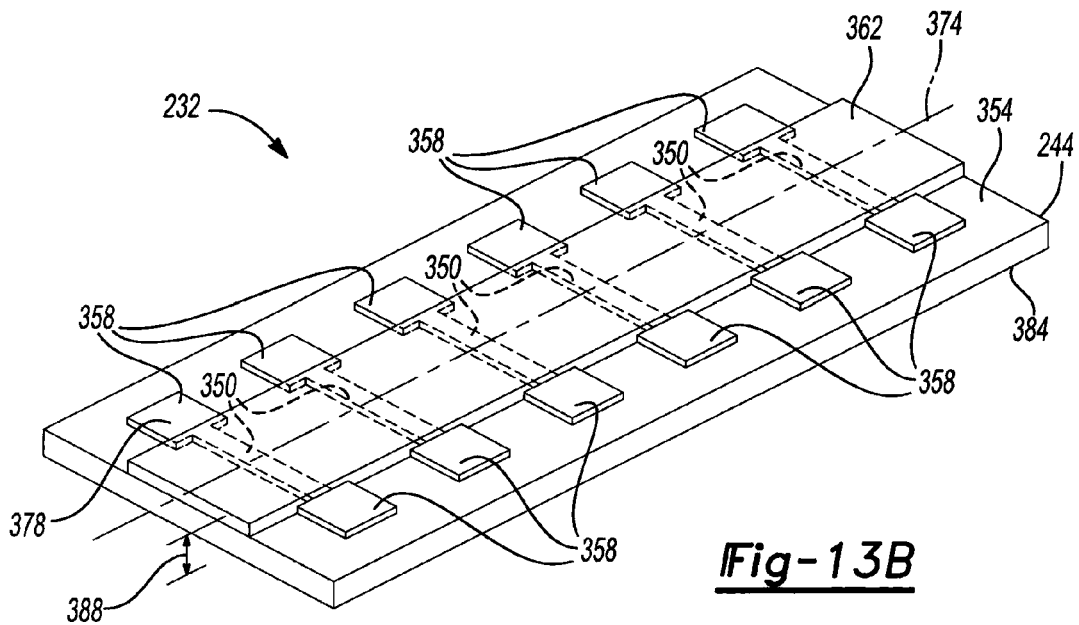
FIG. 13B is a perspective view of the flexible printed circuit sheet of FIG. 13A in an exemplary assembled configuration according to the principles of the present disclosure.

The coupling pads 358 can be positioned or printed at ends of the copper traces 350, as can be seen in FIGS. 13A-13B. The coupling pads 358 can be formed in any desired shape, including the square or substantially square shape 378 shown, for example, in FIGS. 13A-13B. The coupling pads 358 can also be formed to have varying dimensions, including a dimension or dimensions that is/are larger than a typical outer diameter of the wires that are to be coupled to the pads. As discussed above, such a greater dimension of the coupling pads 358 relative to the size of the wire can provide for easier soldering of the wires to the pads 358 and thus reduce time and manufacturing complexity associated with building an instrument requiring termination of fine gauge wires.

For example, the exemplary coupling pads 358 shown in FIGS. 13A-13B are square in shape and include a length and width of approximately 0.5 mm. Again, it should be appreciated that the length and width of coupling pads 358 can vary depending on the particular application of flexible printed circuit sheet 232. The coupling pads 358 can also be formed from copper and include a tinning material, such as tin/lead, nickel/gold and/or gold.

The insulative layer 362 can be positioned over the copper traces 350 and coupled to the base layer 244 in any suitable manner that allows or does not inhibit the flexibility and conformability of the flexible circuit sheet 232. In one exemplary configuration, the insulative layer 362 can be adhered to the base layer 244 and copper traces 350 with an adhesive. The insulative layer 362 can include a shape and/or width so as to cover or substantially cover the copper traces 350 between the coupling pads 358 to insulate the traces 350 from external contact. Similar to the base layer 244, the insulative layer 362 can also be formed from a polymeric material, such as polyimide. In one exemplary configuration, the insulative layer 362 can be a photoimageable coverlay. As will be discussed in greater detail below, the insulative layer 362 can include a thickness that is less than a thickness of the base layer 244. In the exemplary configuration shown in FIGS. 13A-13B, the insulative layer 362 can include a rectangular shape corresponding to the exemplary symmetrical positioning of the copper traces 350 and corresponding coupling pads 358.

To couple the flexible printed circuit sheet 232 to a structure, such as the exemplary instrument 100, an adhesive 364 can be used. It should be appreciated, however, that other means for securing the flexible circuit sheet 232 to a structure can be used, so long as the means used does not inhibit the flexible nature of printed circuit sheet 232. In one exemplary configuration, the adhesive 364 can be applied to a lower or second side 384 of base layer 244. In this regard, the second side of base layer 244 can be substantially smooth. It should also be appreciated that the adhesive 364 can also be applied to the structure in addition to or in lieu of being applied to base layer 244. In one exemplary configuration, the adhesive 364 can include a medical grade pressure sensitive adhesive. In another exemplary configuration, the adhesive 364 can include a medical grade liquid or gel adhesive.

The exemplary flexible printed circuit sheet 232, in the exemplary assembled configuration shown in FIG. 13B, can include a bound together or overall thickness 388 of between approximately 0.04-0.07 mm. In some exemplary embodiments, the overall thickness 388 can be only approximately 0.04 mm. Stated another way, the assembled base layer 244, circuit traces and pads 350, 358 and insulative layer 263 can include an overall thickness 388 of approximately 0.05 mm. It should be appreciated, however, that such a thickness can vary to be smaller or larger depending on the particular application of the flexible printed circuit sheet 232. Use of the pressure sensitive adhesive 364 can increase the overall thickness 388 by approximately 0.025 mm to 0.05 mm. Similarly, use of the gel or liquid adhesive can increase the thickness 388 by only 0.01 mm. Thus, the overall thickness 388 of the flexible printed circuit sheet 232, in various different configurations, can vary from 0.04 mm (without adhesive 364) to approximately 0.11 mm (with adhesive 364). As discussed above, such a minimal thickness 388 of flexible circuit sheet 232 provides for not only flexibility and conformability of the circuit sheet 232, but also applicability of the flexible circuit sheets to medical and other devices and/or instruments that have very tight volume and/or packaging constraints.

For example, one of ordinary skill in the art will appreciate that conventional printed circuit boards considered thin in the industry can include a thickness of 0.8 mm or greater and can be made from dielectric layers laminated together with epoxy resin prepreg. Such materials combined with such a thickness do not provide for the conventional circuit boards being flexible and thus they cannot conform to non-planar surfaces and/or flex such that they cannot be used with a flexible or malleable medical instrument. Further, such a thickness of 0.8 mm or greater can preclude use of conventional printed circuit boards in medical instruments or devices where maintaining a minimum thickness or overall height is a critical parameter.

The very thin thickness 388 of the exemplary flexible circuit sheet 232, together with the polyimide material construction, can provide for significant flexibility and/or conformability of circuit sheet 232. In this regard, the exemplary flexible circuit sheet 232 having the overall thickness 388 and polyimide material construction can include a bend radius of approximately ten times the thickness 388. Thus, for the exemplary configuration of flexible circuit sheet 232 discussed herein, the bend radius can be approximately 0.4 mm to 0.7 mm depending on the overall thickness 388 of the flexible printed circuit sheet 232. Such a bend radius can provide for significant flexibility in conforming the flexible printed circuit sheet to or around tight radii associated with compact or low profile medical instruments or devices.

Figure 14:
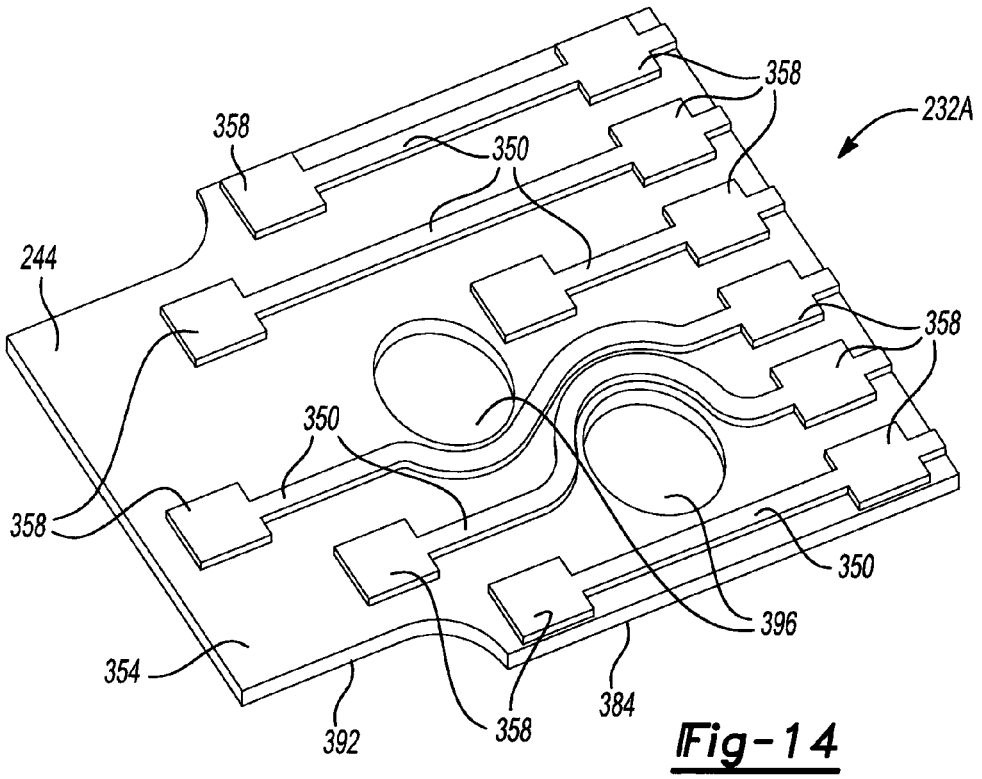
FIG. 14 is a perspective view of another exemplary flexible printed circuit sheet according to the principles of the present disclosure.

With additional reference to FIGS. 14-16, another exemplary flexible printed circuit sheet 232 will now be discussed and designated with reference numeral 232A. Flexible printed circuit sheet 232A can include similar properties and thickness dimensions as discussed above for flexible circuit sheet 232 such that like reference numerals refer to like features or components. Flexible printed circuit sheet 232A is shown having an exemplary custom shape 392 configured for a particular medical instrument or device. In the exemplary configuration illustrated in FIGS. 14-16, flexible printed circuit sheet 232A can include one or more apertures 396 configured to be positioned around and/or provide access to corresponding coil assemblies 214. The copper circuit traces 350 can be printed in various patterns to accommodate the apertures 396 and custom shape 392, as shown for example in FIG. 14. It should be appreciated that while not shown for clarity purposes, the insulative layer 362 can be custom shaped to include appropriate cutouts and an appropriate shape to cover the copper traces 350 while leaving the coupling pads 358 of flexible circuit sheet 232A exposed.

Figure 15:
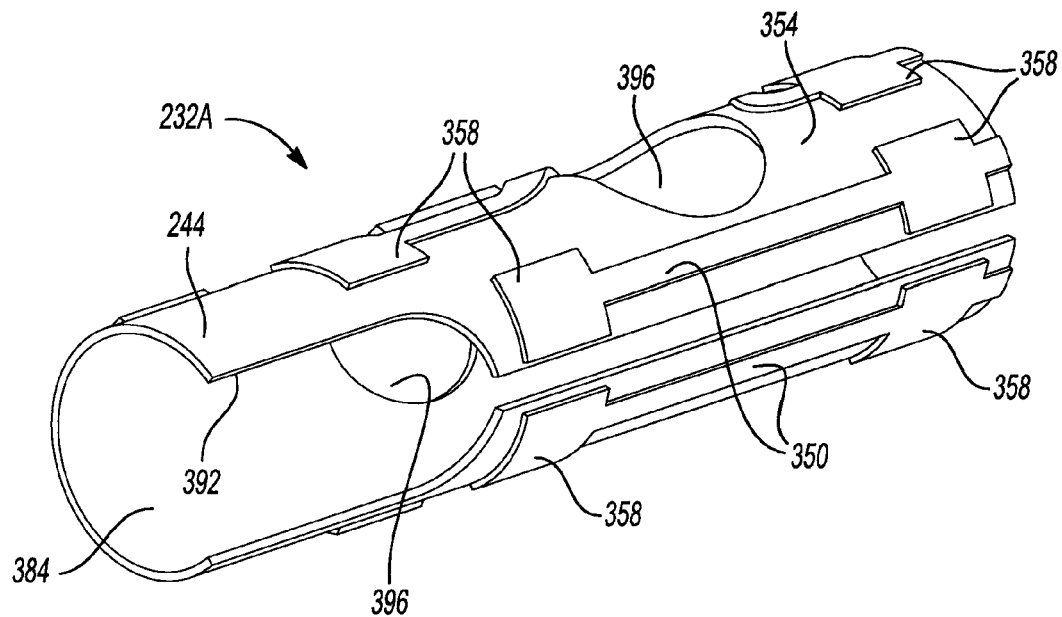
FIG. 15 is a perspective view illustrating the flexible printed circuit sheet of FIG. 14 in a bent or flexed condition according to the principles of the present disclosure.
Figure 16:
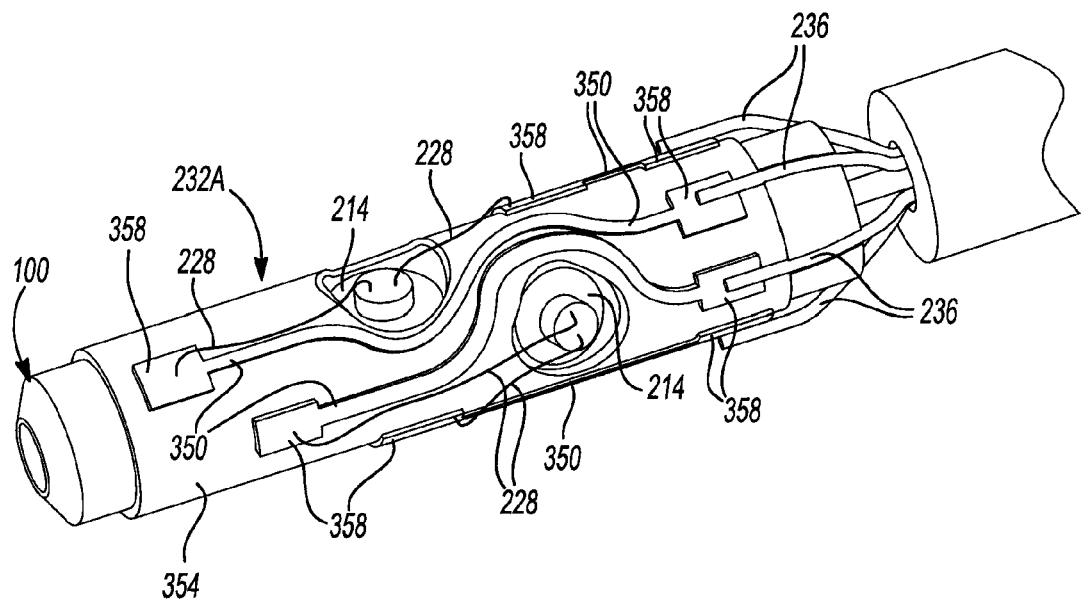
FIG. 16 is a perspective view of the flexible printed circuit sheet of FIGS. 14 and 15 in a flexed condition conforming to an outer surface of an exemplary instrument according to the principles of the present disclosure.

As can be seen in FIGS. 15-16, the flexible printed circuit sheet 232A can be bent or flexed in various configurations to conform to various instrument or device shapes, such as the distal end of a malleable instrument 100. In one exemplary configuration, the flexible printed circuit sheet 232A can wrap around or substantially around the malleable suction instrument 100. The flexible printed circuit sheet 232A can also bend, flex or twist with the malleable suction instrument 100 during use thereof. In this regard, the flexible printed circuit sheet 232A can flex three-dimensionally. In the exemplary configuration shown in FIG. 16, flexible circuit sheet 232A can be adhered to the outer surface of a component of malleable suction instrument 100 using, for example, adhesive 364. As discussed above, the lead wires 236A can be electrically coupled, such as via soldering, to the appropriate coupling pads 358 and the coil assembly wires 228 can be soldered to the corresponding pads 358, as also shown in FIG. 16.

Figure 17:
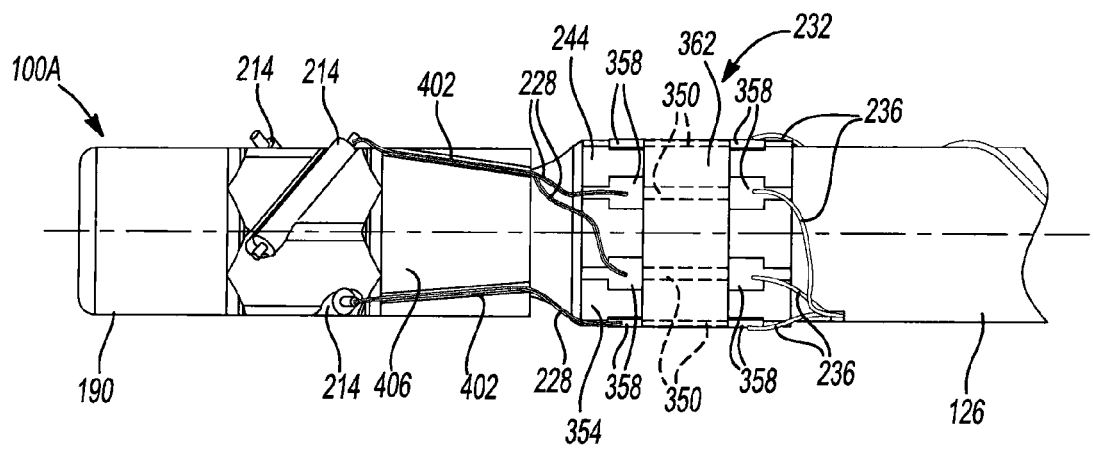
FIG. 17 is a partial side view of the distal region of the exemplary suction instrument of FIG. 5 associated with the exemplary flexible circuit sheet and having wire management channels according to the principles of the present disclosure.

Turning now to FIG. 17, flexible printed circuit sheet 232 is shown adhered to malleable suction instrument 100A, which is substantially similar to malleable suction instrument 100 shown in FIG. 5, except for channels 402 formed in sleeve 190. Channels 402 can receive sensor or coil wires 228 and provide a predetermined routing placement for wires 228 relative to instrument 100A, as well as position wires 228 below an outer surface 406 of sleeve 190. Flexible printed circuit sheet 232 can conform to an outer surface of malleable suction instrument 100A and can provide for efficient and cost effective termination of coil assembly wires 228 and lead wires 236, as shown for example in FIG. 17. For example, flexible circuit sheet 232 can be flexed to correspond to a radius of the outer surface of the instrument so as to lay substantially flush or coplanar to the outer surface.

Figure 18:
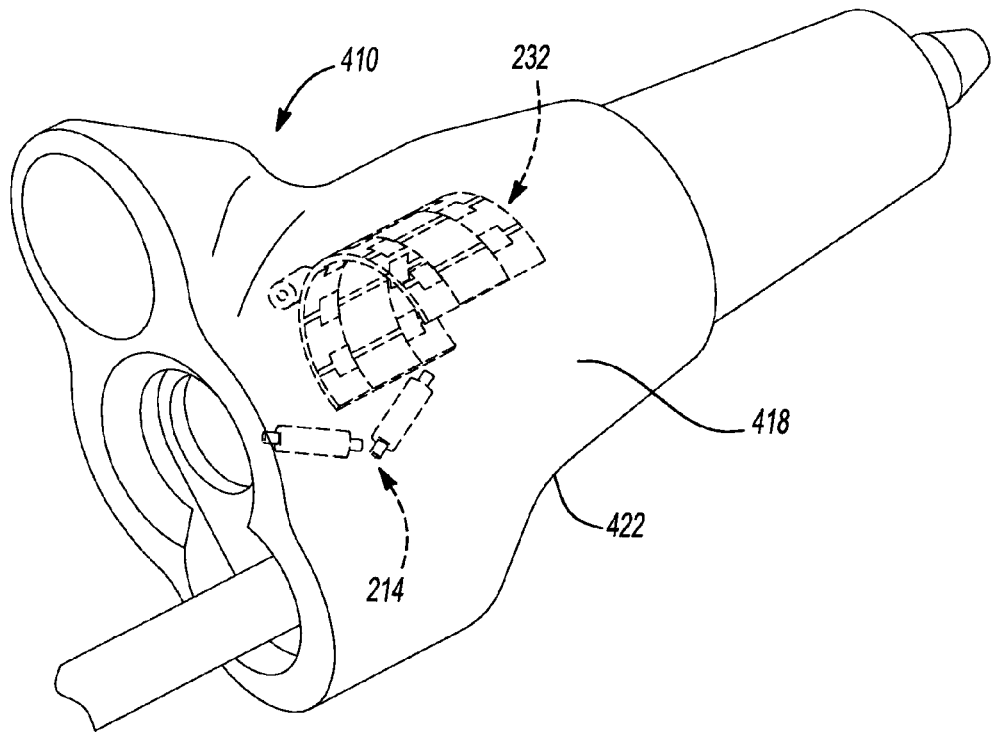
FIG. 18 is a perspective view of a patient tracking device having an exemplary flexible printed circuit sheet and associated coils according to the principles of the present disclosure.

With particular reference to FIG. 18, flexible printed circuit sheet 232 is shown associated with an electromagnetic patient tracker device 410. In the exemplary configuration illustrated, tracker device 410 can include the three coil assemblies 214 positioned equidistant circumferentially around a longitudinal axis 414 of tracker device 410 and can be configured to communicate with and be tracked by EM tracking system 60 of navigation system 10. The coils assemblies 214 can also be positioned, in the exemplary configuration illustrated, at an angle, such as between forty-five degrees and fifty-five degrees relative to axis 414 in a similar manner as coil assemblies 214 are positioned relative to instrument 100 shown in FIG. 5. It will be appreciated, however, that various other coil assembly 214 configurations and/or orientations can be utilized with patient tracker 410.

The flexible printed circuit sheet 232 can be positioned inside of or within a body 418 of tracker 410 as shown in FIG. 18, or could alternatively be positioned on an outer surface 422 of tracker 410. In one exemplary configuration, flexible printed circuit sheet 232 can be bent or flexed to conform to the shape or contour of the surface it will be adhered to, as shown in FIG. 18. Sensor and lead wires (not shown for clarity) can be soldered to the respective circuit pads in the manner discussed above.

Turning now to FIGS. 19 and 20A-20C, another exemplary configuration of a flexible printed circuit sheet is shown at 232B. Flexible printed circuit sheet 232B can be similar to flexible printed circuit sheet 232A such that like reference numerals refer to like components or features and only differences will be discussed in detail. Similar to flexible printed circuit sheet 232A, the flexible printed circuit sheet 232B can include base layer 244 having upper surface 354, conductive traces 350, solder or coupling pads 358 and top insulative layer 362.

Figure 19:
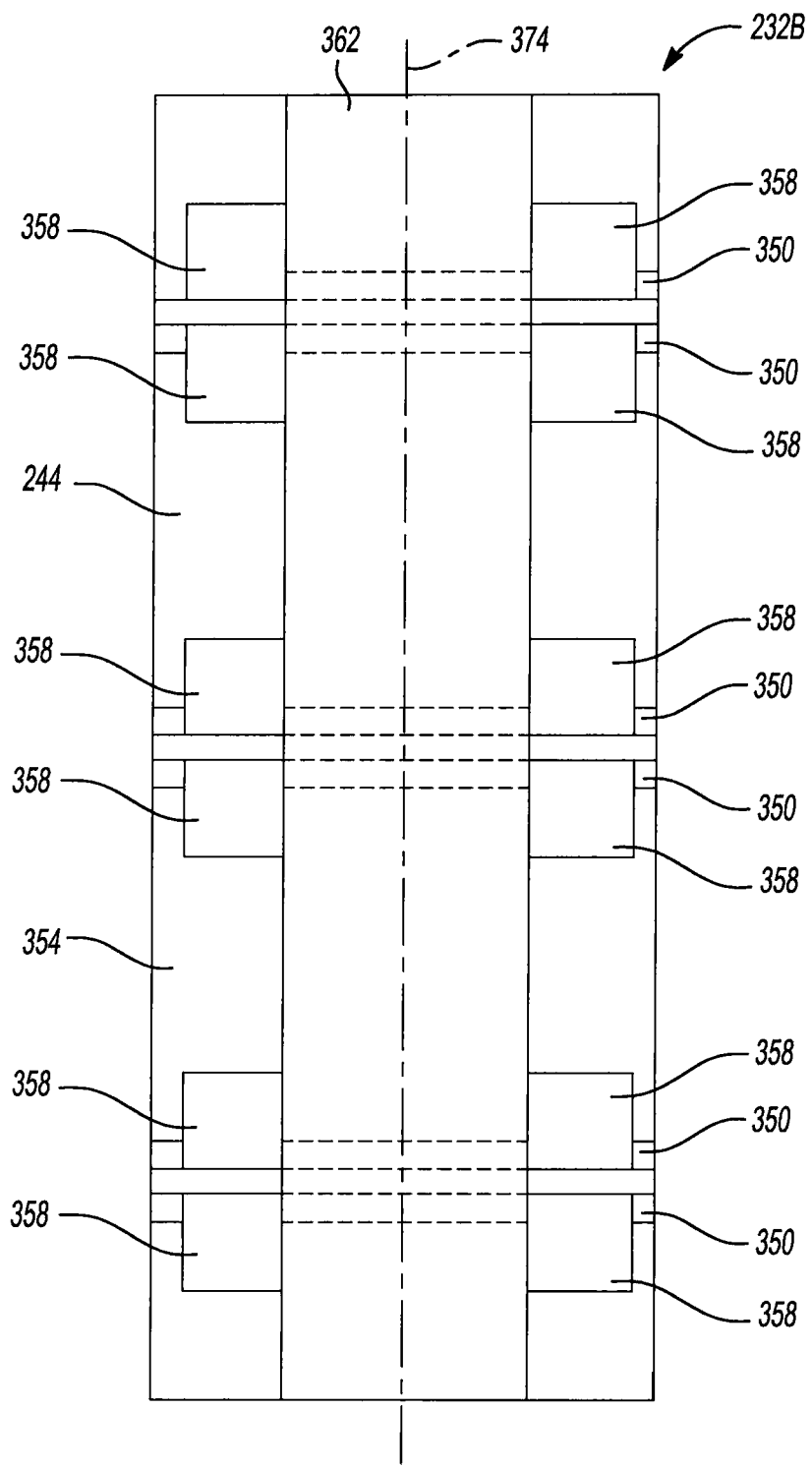
FIG. 19 is a top view of another exemplary flexible printed sheet according to the principles of the present disclosure.

The flexible printed circuit sheet 232B can include one or more paired circuit traces where the pairs of circuit traces are closely spaced together, as shown for example in FIG. 19. By positioning the circuit traces in such a manner along the longitudinal axis 374, any electromagnetic interference and/or pickup from an associated electromagnetic navigation system can be minimized. In this exemplary configuration, the conductive traces 350 can be parallel or substantially parallel to each other and spaced apart by less than 0.3 mm, including 0.23 mm, in each pair of circuit traces. However, it should be appreciated that other spacing may be utilized depending on design and other variables.

Figure 20A:
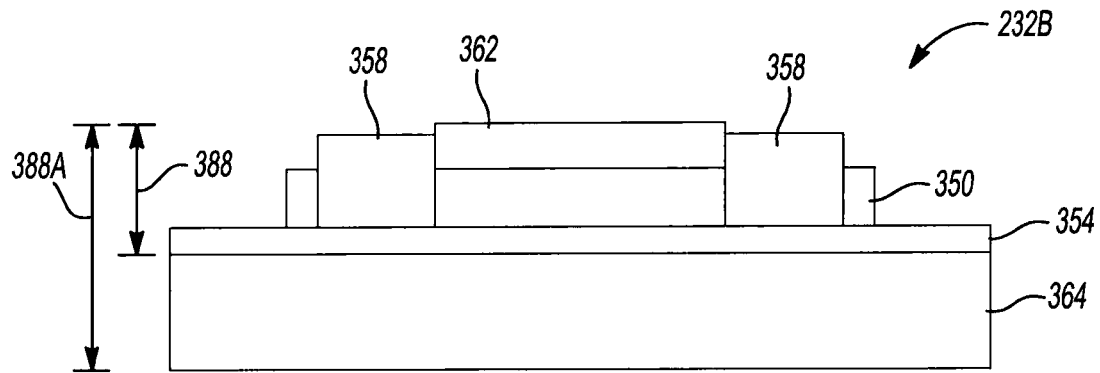
FIGS. 20A-20C are side views representing various exemplary configurations of the flexible printed circuit sheet of FIG. 19 according to the principles of the present disclosure.
Figure 20B:
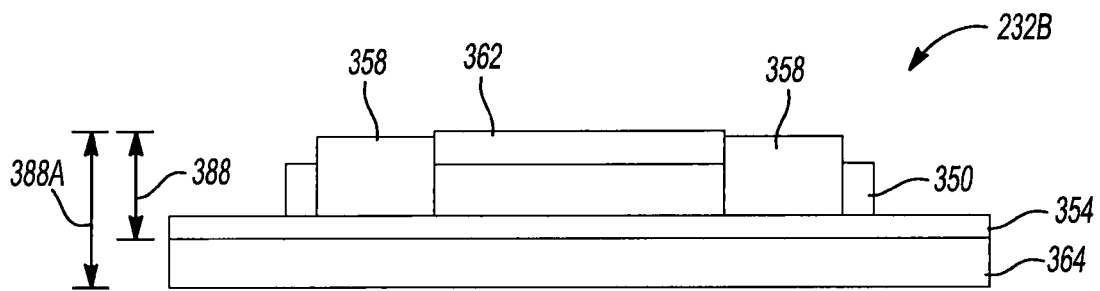
Figure 20C:
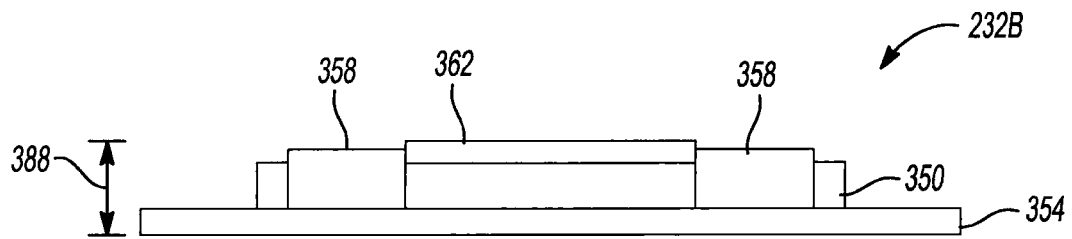

With particular reference to FIGS. 20A-20C, three exemplary configurations (shown in side views) of the flexible printed circuit sheet 232B are shown. In these exemplary configurations, various different thicknesses of the flexible printed circuit sheet 232B are shown with and without adhesive, as will be discussed in greater detail below.

Referring to FIG. 20A, flexible printed circuit sheet 232B is shown in a configuration utilizing adhesive 364. In this configuration, the base layer 244 can include a thickness of approximately 0.01 mm, the conductive traces and pads 350, 358 can include a thickness of approximately 0.04 mm and the insulative layer 362 can include a thickness of approximately 0.02 mm. In the assembled configuration, the flexible printed circuit sheet 232B shown in FIG. 20A can include an overall thickness 388 of approximately 0.07 mm without adhesive 364 and an overall thickness 388A of 0.11 mm with adhesive 364.

With reference to FIG. 20B, the flexible printed circuit sheet 232B is shown having a smaller overall thickness 388 of approximately 0.05 mm without adhesive 364 and an overall thickness 388A of 0.07 mm with adhesive 364. In this configuration, the base layer 244 can similarly have a thickness of approximately 0.01 mm, the conductive traces and pads 350, 358 can include a thickness of approximately 0.02-0.03 mm and the insulative layer can include a thickness of approximately 0.01 mm.

Referring now to FIG. 20C, the flexible printed circuit sheet 232B is shown in another exemplary configuration having an overall thickness 388 of approximately 0.04 mm. In this configuration, adhesive 364 may not be utilized. In such a configuration where adhesive 364 is not utilized, a heat shrink layer over the flexible printed circuit sheet 232B can optionally be utilized to couple flexible printed circuit sheet 232B to an instrument, such as the suction instrument 100 discussed above. In this configuration of flexible printed circuit sheet 232B, the base layer 244 can also include a thickness of approximately 0.01 mm, the conductive traces and pads 350, 358 can include a thickness of approximately 0.01-0.02 mm, and the insulative layer 364 can include a thickness of approximately 0.01 mm.

Figure 21:
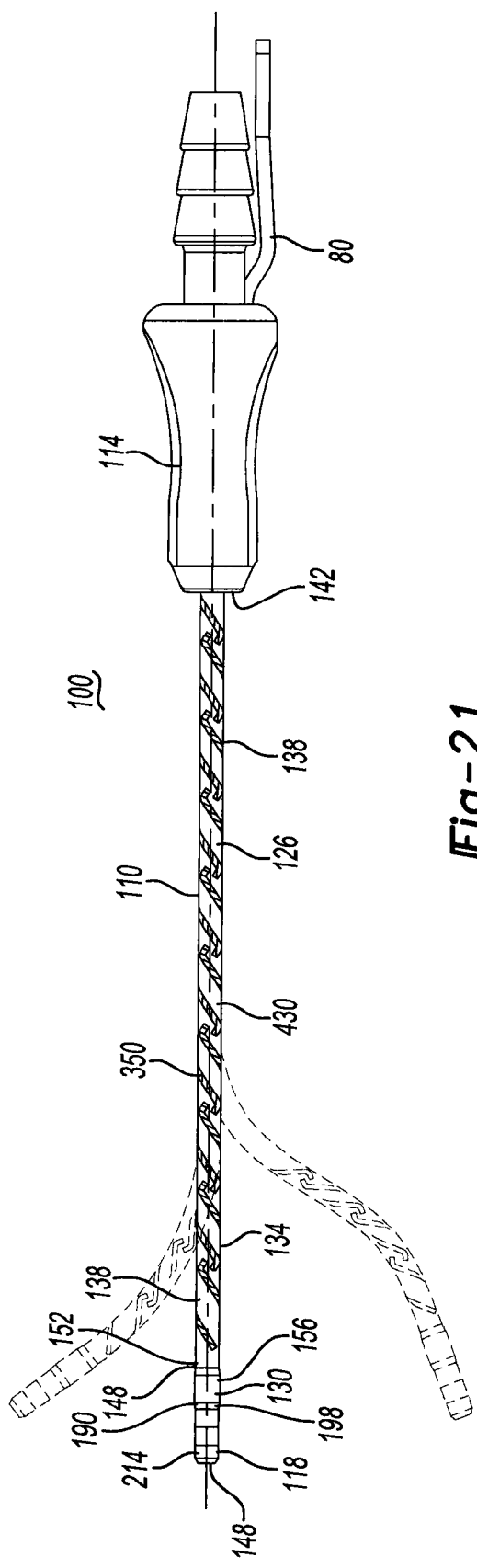
FIG. 21 is a top plane view of an exemplary surgical instrument for use with a navigation system according to the principles of the present disclosure.

Referring now to FIG. 21, an alternate surgical instrument 100 will be described in greater detail. Similar reference numerals will be used to describe similar structures shown in FIGS. 2-4. In one exemplary configuration, the surgical instrument 100 can be a malleable tool used for suction, including fluid and tissue removal in ENT procedures. Associated with the surgical instrument 100 is a flexible circuit 430 to transport electrical signals between the navigation probe interface 80 and a plurality of navigation coils 214. The flexible circuit 430 provides termination pads (not shown) for fine coil wires as well as cable wires and conductive traces 350 to bring electric connectivity to portions of the surgical instrument 100. As described further below, the conductive traces 350 are configured to minimize the pickup of stray electromagnetic noise.

The flexible circuit 430 described in detail below can be usable in other tracked medical devices or any other devices where tracking or navigating a distal tip of a device is desired. Thus, while the following description continues with reference to a navigated surgical instrument 100, the discussion is also applicable to the surgical instruments discussed above and any other appropriate instruments that require tracking or navigation of instruments that require substantially smooth exterior surfaces so as to not adversely interact with patient tissue. This is in contrast to existing instruments that have discrete wires wrapped around the outside of the instrument causing a ribbed effect. For example, the flexible circuit can be used in a micro coil based core tracker assembly, slanted coil based cranial stylets, biopsy needles, or other navigated instruments requiring challenging volumetric packaging constraints.

Surgical instrument 100 can include a tube assembly 110, a handle assembly 114, and a tracking sensor arrangement 118. Surgical instrument 100 or portions thereof can be configured for a single use such that it would be disposed of after such use. The tube assembly 110 can include a malleable elongated tubular body 126 and an insert portion 130. The malleable tubular body 126 can be formed from a malleable metallic material such that the tubular body 126 body portion can be bent between the proximal and distal ends from a first configuration to a second bent configuration and maintain the bent configuration.

The tubular body 126 can include an outer diameter 134 and an inner diameter 138 and can have a first or proximal end 142 coupled to the handle assembly 114 and a second opposite or distal end 148 configured to receive insert portion 130. As best seen in FIG. 4, the second end 148 can include an internal annular recess 152 having an inner diameter 156 greater than the inner diameter 138 of the remaining portion of body 126. The body 126 can also be provided in various lengths and diameters including, by way of example, lengths from 50 mm-500 mm and including 7, 9 and 12 French diameters. The insert portion 130 can be configured to provide non-malleable support for at least the tracking sensor 84.

Insert portion 130 can include a sleeve 190 received on an exterior thereof. Sleeve 190 can include an inner diameter 194 substantially equal to the outer diameter of insert portion 130, and an outer diameter 198 substantially equal to the outer diameter 134 of body 126. The insertion of the sleeve 190 into the first end 148 of the body can facilitate the electronic coupling of tracking coils with the navigation system. Alternatively, electronic coupling can be accomplished using soldering techniques. It should be appreciated that sleeve 190 can also be configured with different diameters relative to body 126.

Figure 22:
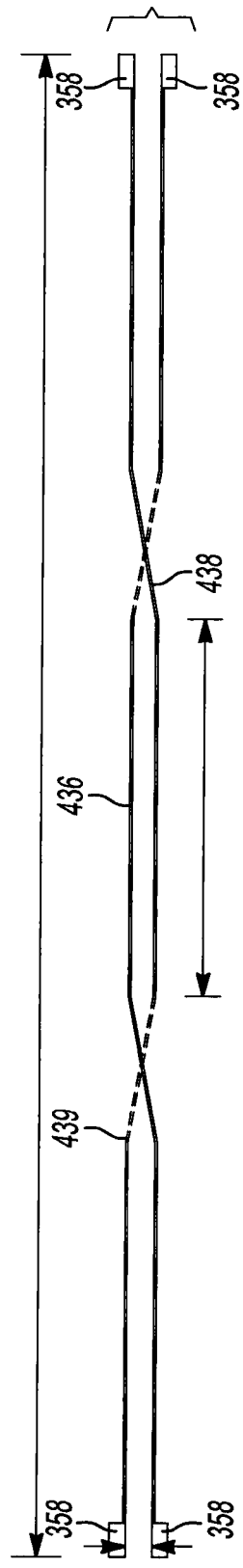
FIG. 22 represents a top view of traces associated with the flexible circuit sheet of FIG. 23B.

FIG. 22 represents a top view of conductive traces 436, 438 associated with the flexible circuit 430 of FIG. 21. The conductive traces 436, 438 are twisted to form loops configured to have opposite handedness from its nearest neighbors. The alternative handedness effectively cancels electromagnetic noise. In this regard, the twisted pairs minimize electromagnetic pickup that would degrade navigation performance. The twisted pair configuration is formed using through-substrate or base layer 434 connections, as is illustrated exemplarily in FIG. 24D on the flexible base layer 434, and provides the needed form factor. In this regard, the flexible circuit 430 protrudes from the nominal surface radius of the body portion 126 by less than about 0.05 mm, thus minimizing interaction of the device with patient tissue. In other words, the thickness of the flex circuit is 0.08 mm which is less than the thickness of the twisted wires 0.4 to 0.5 mm. The conductive traces 436, 438 have first and second coupling pads 350 and 358 disposed at a first proximal end 142 and a second set of coupling pads 350 and 358 disposed at the second distal end 148, wherein the length of the flexible circuit 430 extending from the first proximal end 142 to the second distal end 148 is of the elongated body 126. Furthermore, the profile of the construction utilizing the flexible circuit 430 is substantially smoother and more uniform than the ribbed profile of the twisted wire configuration.

Figure 23A:
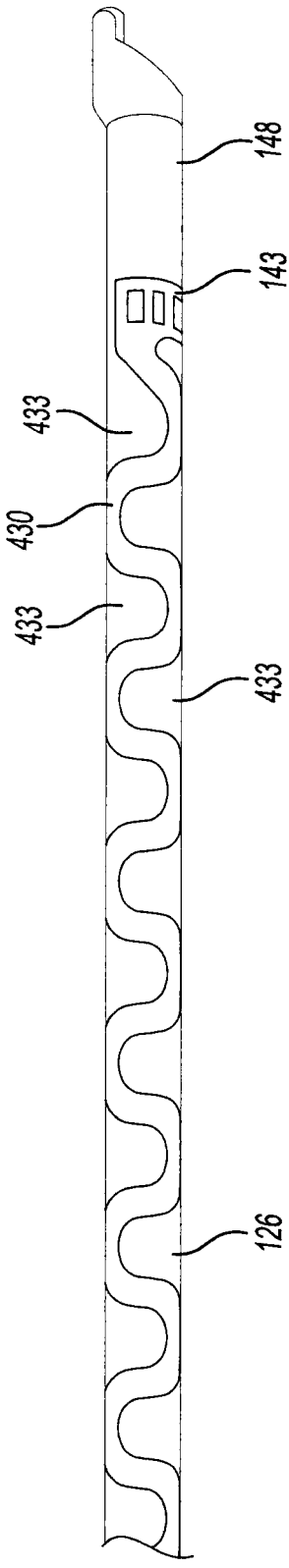
FIG. 23A represents a malleable suction tube shown in FIG. 21.
Figure 23B:
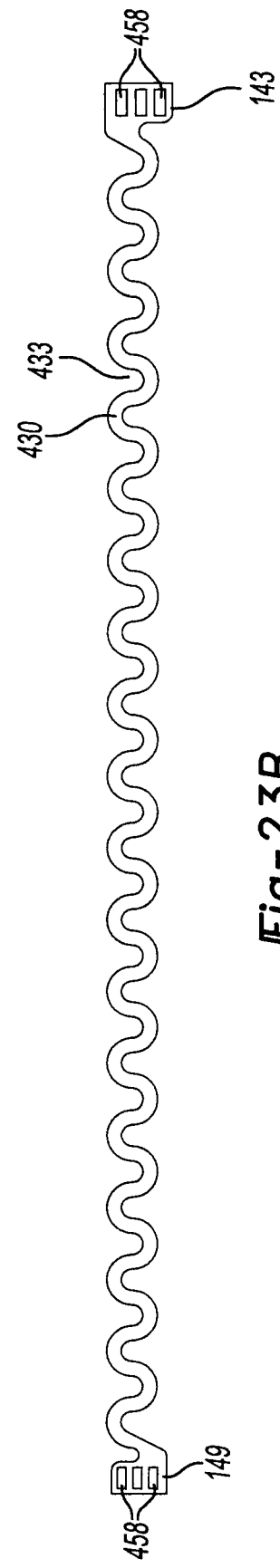
FIG. 23B represents a conformed flexible circuit shown in FIG. 22A.

With particular reference to FIGS. 23A and 23B, the flexible circuit 430 having one or more, including three pairs of conductive traces 436, 438 as illustrated in FIG. 22 is shown. The flexible circuit 430 is generally disposed around the body portion 126 and extends from the tracking device 84 from the second distal end 148 to the first proximal end 142 and handle assembly 114. The flexible circuit is configured to conform to the bent configuration of the body portion 126 such that it does not strain or break during bending of the body portion 126. The flexible circuit 430 can be longitudinally or helically disposed around a portion of the body portion 126 from the tracking device 84 to the handle assembly 114. If longitudinally disposed, the flexible circuit is curved transverse to the longitudinal axis of the flexible circuit 430 to conform to the curvature of the instrument shaft, as shown in FIG. 23A. The flexible circuit 430 can have a sinusoidal periphery or have a periphery formed of a plurality of curved line segments. If helically disposed, the flexible circuit 430 is wrapped helically around the longitudinal axis as is shown in FIG. 21. To allow the body portion 126 to curve when the flexible circuit 430 is wound around the body portion 126, the flexible circuit can define gaps 433 which allow and accommodate for compression and tension of an external surface of the body portion 126. When the outer portion of the body portion 126 is in tension, the gaps 433 can expand, while the inner portion during the bending of the body portion 126.

FIG. 23A represents the malleable tube 110 shown in FIG. 21. As shown, the flexible circuit 430 extends from the first proximal end 142 of the body portion 126 to the second distal end 148 of the body portion 126. A serpentine shaped flexible circuit 430 is laid longitudinally wrapped around the body portion 126. As described below, the conductors in the flexible circuit 430 can be generally parallel (see FIG. 24F) or form twisted pairs (See FIG. 24A) to allow the navigation system to properly account for electromagnetic noise. Each twist in the twisted pair produces a small loop to reduce electromagnetic coupling noise.

FIG. 23B represents the flexible circuit 430 in a planar manner before it has been conformed as is shown in FIG. 23A. The serpentine shaped flexed circuit 430, when wrapped around the body portion 126, defines the gaps 433 along edges of the flexible circuit. It is envisioned the maximum radius of curvature of the body portion 126 may be regulated by the size and positions of the defined gaps 433.

FIGS. 24A-24O represent perspective views of exemplary configurations of the flexible circuit 430 according to the present teachings. Generally, the flexible circuit 430 has the first and second conductive traces 436, 438 which are parallel or are twisted to reduce the influence of electromagnetic noise on the tracking system. The flexible circuit 430 can have a base layer 434 formed of a thin insulative material such as polyimide, polyethylene, terephthalate, latex, nitrile rubber, polysiloxanes, silicone, polyurethane, polyether block amide (trade name PEBAX), a first circuit trace 436 having a first upper portion 460 of the trace formed on a first upper side 441 of the base layer 434, and a second circuit trace 438 having a second lower portion 462 formed on an second lower side 442 of the base layer 434. The flexible circuit 430 can take any number of shapes which allow the flexible circuit 430 and medical device to bend.

The base layer 434 and insulative layers include material properties and a thickness configured to facilitate the flexible circuit 430 being flexible such that the flexible circuit 430 is adapted to conform to an exterior surface of the elongated body 126, as well as allow the elongated body 126 to bend along the longitudinal axis of the body portion 126. The flexible circuit 430 can have various components disposed between the proximal and distal ends 143, 149. In this regard, various electrical components such as amplifier or tracking coils can be attached. For example, coil assemblies 214 can be coupled to the flexible circuit 430 at predetermined locations between the proximal and distal end 143, 149. In other words, a single coil assembly can be located at the second distal end 149, multiple coils can be located along the length of the flexible circuit 430.

As shown in FIG. 24A, the conductive traces 436, 438 can form a twisted pair configuration. The first trace 436 runs along the first upper side 441 and crosses over a second trace 438 positioned on an opposite second side 442 at an acute angle A. The first trace 436 then passes through the insulator or base layer 434 and runs along the second lower side 442. A second trace runs along the second lower side 442 and crosses over a first trace 436 positioned on the first upper side 441 at the acute angle A. The first and second conductive traces 436, 438 cross from over to under at electrical vias 439. The vias 439 extend transversely through the base layer 434 to connect the conductive trace from the first upper side 441 to the second lower side 442.

FIGS. 24B and 24C represent a flexible circuit 430 having three twisted pair configurations as shown in FIG. 24A as they would be wrapped around an elongated body 126. As shown, coupling pads 358 are provided for coupling to the leads of three coils at the second distal end 149 or to the coupling cable wires at the first proximal end 143. The vias 439 are disposed between the overlapping conductive traces 436, 438 were the traces are located on opposite sides of the base layer 434. Generally, the conductive traces 436, 438 are positioned adjacent and parallel to each other to minimize conductor loop size.

As shown in FIG. 24D, the loop area 446 can be reduced by placing the first trace 436 directly over the second trace 438 on the base layer 434 for a majority of the length of the trace except where the conductive traces separate to form vias 439 in passing areas 448. In other words, for short distances, the conductive traces separate enough to allow the traces to pass through the base layer 434 to the other side. At this point, the traces return to a position where they are parallel to each other. The loop area can further be reduced by reducing the thickness of the insulative base layer 434. It is envisioned the base layer 434 can have a thickness of about 0.025 mm. The base layer 434 can be formed of polyimide, polyethylene, terephthalate, as well as a thin elastic insulative base layer 434. The base layers 434 can be latex, nitrile rubber, polysiloxanes, silicone, polyurethane, polyether block amide or PEBAX.

As shown in FIG. 24E, by using multiple base or insulative layers, and placing oppositely handed twisted pairs intertwisted with an adjacent pair of conductors, further noise cancellation can be accomplished. The oppositely handed twisted pairs connect in parallel, adding redundancy to this canceled double twisted pair configuration. As previously discussed, conductive traces 436, 438 are periodically passed through from a first upper side 441 of the base layer 434 to a second lower side 442 of the base layer 434 to form the twisted configuration. As can be see, up to four conductive traces 436, 438 can be separated by insulative layers and run in parallel with the second pair being a twisted pair with opposite handedness to the first pair of conductive traces. These conductive traces are shuttled through various based layers 434 to form the twisted pair constructions.

As shown in FIGS. 24F and 24G, the pair conductive traces 436, 438 need not be in a twisted pair configuration. FIG. 24F depicts a noise minimizing parallel pair set. The configuration uses the thinness of the base layer to minimize noise. FIG. 24G depicts a double oppositely oriented parallel pair with the second pair being a twisted pair with opposite handedness to the first pair of conductive traces. The proximal end 143 of the flexible circuit 430 has a pair of coupling pads 358. The coupling pads 358 are coupled to a pair of parallel conductive traces 436, 438 which are directly over one another, each disposed on opposing sides 441, 442 of the base layer 434. At the distal end 149 of the base layer 434, another pair of coupling pads 358 are provided to couple the flexible circuit to the tracking coils or tracking device 84. In situations where there are numerous conductive traces on the same base layer 434, coupling pads can be found on first and second (top or bottom) sides of the base layer 434. This allows for the convenient coupling of tracking devices to the base layer 434 using soldering or connectors.

Figure 24H:
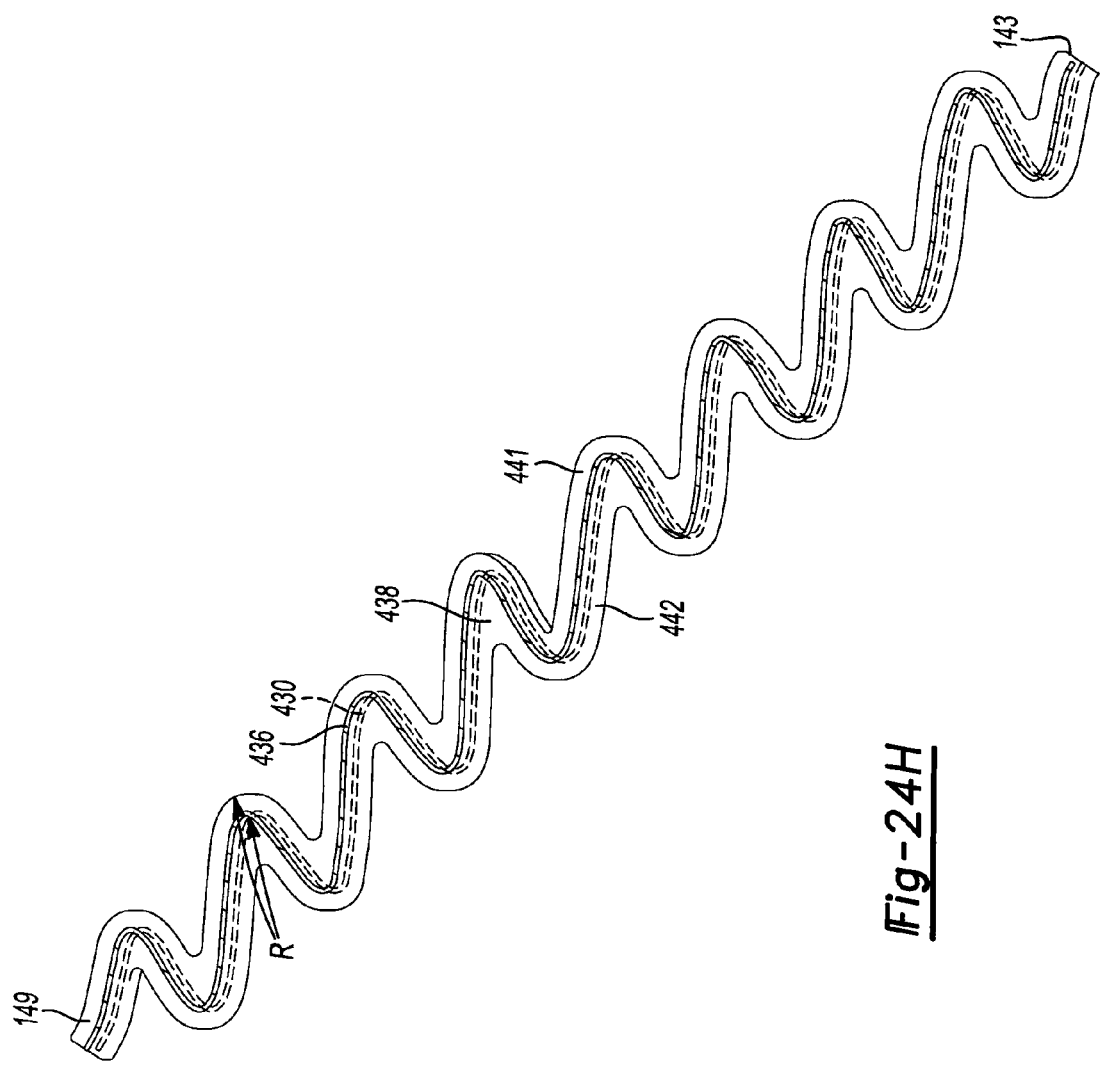
FIGS. 24A-24O represent perspective views of these exemplary configurations of a flexible circuit sheet according to the present disclosure.

As shown in FIGS. 24H-24N, the flexible circuits can have a sinusoidal form. Each conductive trace 436, 438 can be defined on a single side of the base layer 434 and can have radius of curvature R which is between the outer and inner radiuses of curvature of the base layer 434. Alternatively, as shown in FIGS. 24I and 24J, the pairs of conductive traces can be formed in twisted pairs by alternating position on opposite sides of the flexible circuit as described above. The pair crossovers or vias 439 occur at locations along the curve. Generally, the vias 439 are positioned transverse to the longitudinal axis of the body portion 126 or base layer 434. As shown in FIG. 24J, the vias occur at sinusoidal midpoints wherein at FIG. 24I the vias occur at sinusoidal minimums or maximums. The vias 439 are between peaks and valleys in the sinusoidal substrate in order to minimize the mechanical stresses on the electrical vias 439. Generally, the through paths or vias 439 will be formed perpendicular to the longitudinal axis of the tool.

Figure 24K:
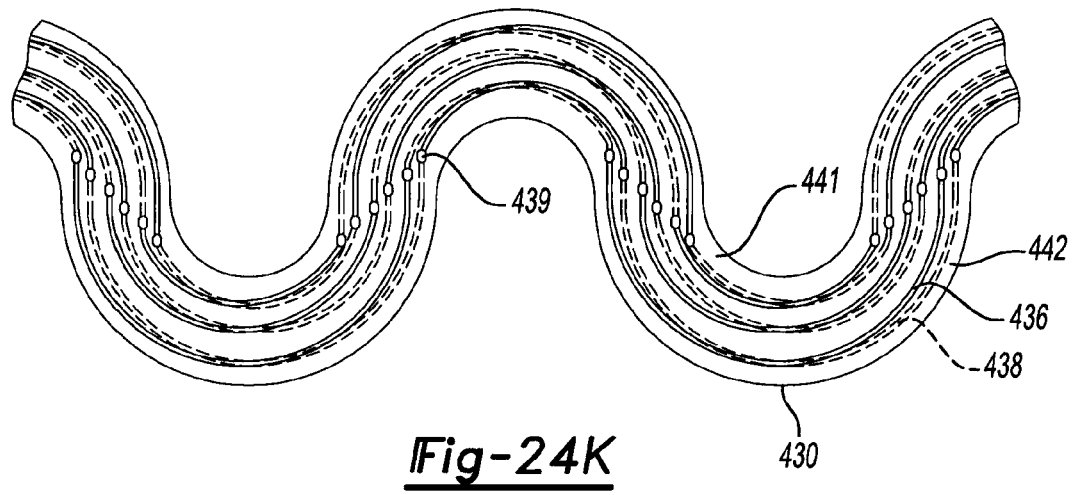
Figure 24L:
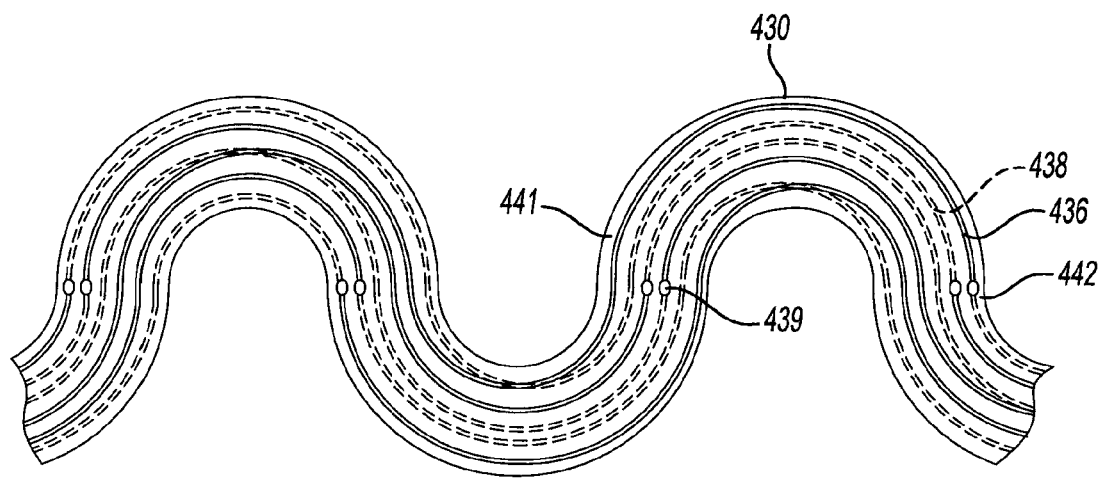

As shown in FIGS. 24K and 24L, three pair of conductive traces can be formed on a single serpentine or sinusoidal shaped base layer 434. In other words, the conductor traces 436, 438 can be three pairs of conductive traces in a single serpentine flexible circuit 430. As can be seen, the position of the vias 439 can be staggered along the length of the flexible circuit so each new curvature represents a new location for the via 439. Alternatively, the vias 439 can be staggered adjacent to the centerline of the flexible circuit.

Figures 24M, 24N:
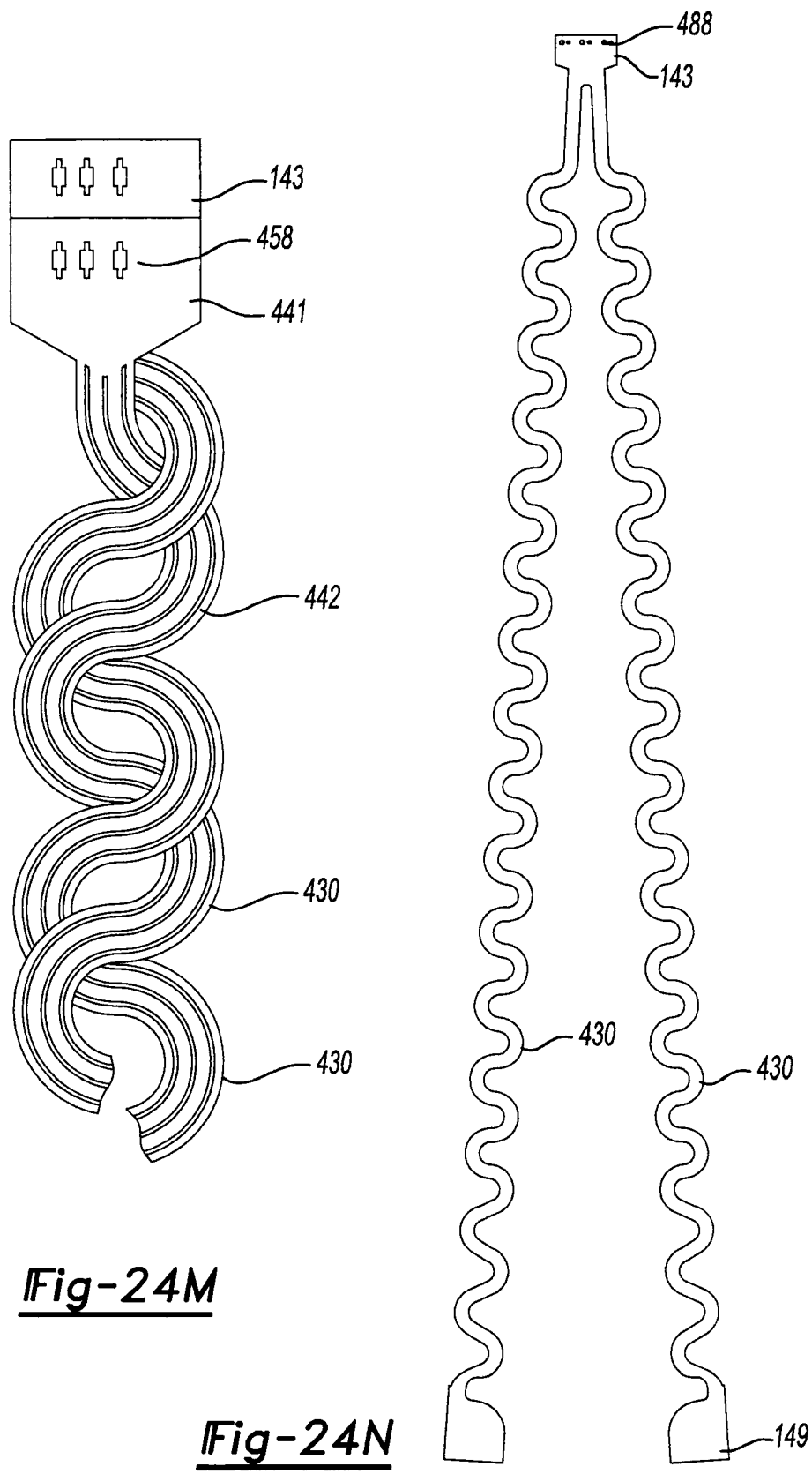
Figure 240:
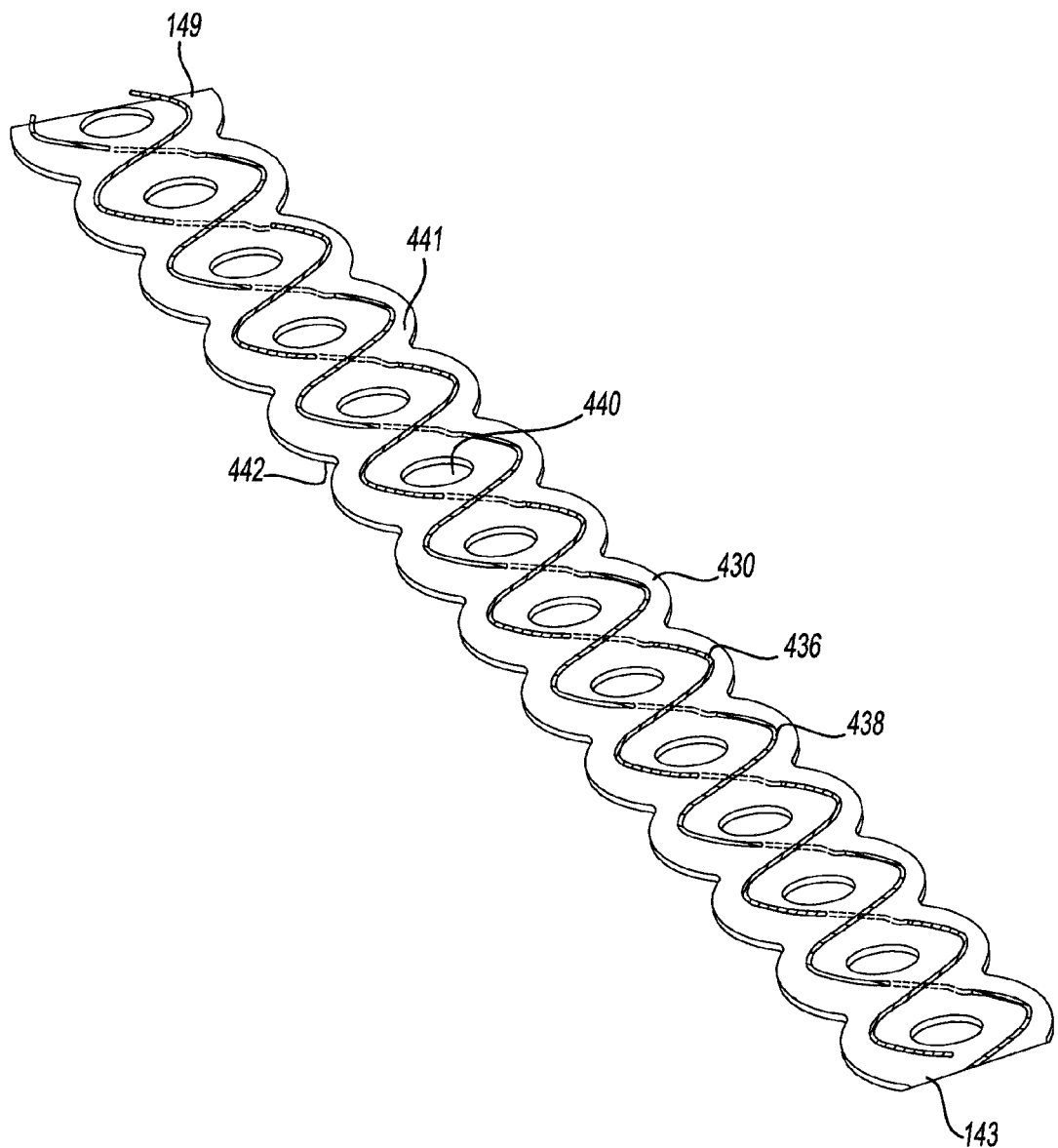

As shown in FIGS. 24M-24N, a pair of serpentine flexible circuits 430 can be braided together to form a flat twisted pair by combining two individual sinusoidal patterned base layers 434, each with three sinusoidally patterned traces explicitly braided into three flat pairs. The base layers 434 can be joined at the proximal end 142 to facilitate the coupling of the tracking device 84. The use of several flexible circuits 430 in this configuration can provide a proper level of rigidity of the body portion 126.

FIG. 24O represents an alternate flexible circuit 430 having a braided pair configuration. The leads 436, 438 are disposed through the base layer and wrapped around apertures 440 defined in the base layer 344. As shown, the base layers 434 form the braided pair configuration and can alternate sides of the flexible circuit 430 as described above.

Figure 25:
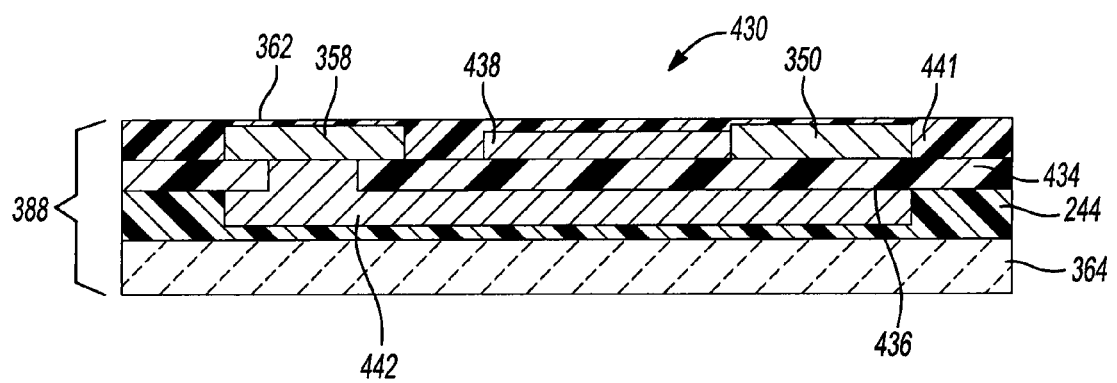
FIGS. 25 and 26 represent cross-sectional views of the flexible circuit sheet shown in FIGS. 24A through 24O.

Referring to FIG. 25, a cross-sectional view of the flexible circuit 430 is shown in a configuration utilizing a pressure sensitive adhesive 364. In this configuration, the base layer 434 can include a thickness of approximately 0.01 mm, the conductive traces 436, 438 and pads 350, 358 can include a thickness of approximately 0.04 mm, and the insulative layer 362 can include a thickness of approximately 0.02 mm. In the assembled configuration, the flexible printed circuit sheet can include an overall thickness 388 of approximately 0.07 mm without adhesive 364 and an overall thickness 388 of 0.11 mm with adhesive 364.

Figure 26:
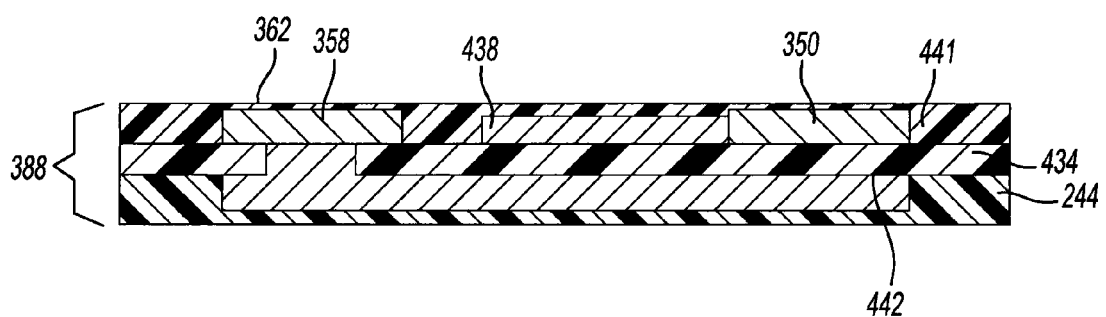

With reference to FIG. 26, the flexible circuit 430 is shown having a smaller overall thickness 388 of approximately 0.05 mm without adhesive 364, and an overall thickness 388 of 0.07 mm with adhesive 364. In this configuration, the base layer 244 can similarly have a thickness of approximately 0.01 mm, the conductive traces 436, 438 and pads 350, 358 can include a thickness of approximately 0.02-0.03 mm, and the insulative layer can include a thickness of approximately 0.01 mm.

It will be appreciated that while various configurations of flexible printed circuit sheets have been discussed herein, other configurations can be utilized taking advantage of the thin, compact and conformable features of such flexible printed circuit sheets. In this exemplary configuration, such a flexible printed circuit sheet could include a length configured to be helically wound from the distal end 148 to the handle assembly 114.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A surgical instrument, comprising:
an elongated body having a proximal end and a distal end;
a tracking device disposed at the distal end; and
a flexible circuit attached to the elongated body and extending from the proximal end to the distal end of the elongated body,
wherein
the flexible circuit is a first flexible circuit that has a sinusoidal periphery,
the flexible circuit has a base layer, a first trace and a second trace,
the first trace and the second trace are coupled to the tracking device,
the first trace and the second trace extend from the proximal end to the distal end,
a first portion of the first trace is on a first side of the base layer,
a second portion of the first trace is on a second side of the base layer
a first portion of the second trace is on the first side of the base layer, and
a second portion of the second trace is on the second side of the base layer.

2. The surgical instrument of claim 1, wherein the flexible circuit protrudes from a surface of the elongated body by less than 0.08 mm.

3. The surgical instrument of claim 1, further comprising pads at the proximal end, wherein the pads are respectively connected to the first trace and the second trace.

4. The surgical instrument of claim 1, wherein first trace and the second trace form a twisted pair.

5. The surgical instrument of claim 1, further comprising an insulative layer formed over the first trace and the second trace to isolate the first trace and the second trace from an external environment,
wherein the base layer and the insulative layer have material properties and a thickness to facilitate the flexible circuit conforming to an exterior surface of the elongated body.

6. The surgical instrument of claim 1, further comprising an outer polymeric shrink fit layer covering the elongated body and the flexible circuit.

7. The surgical instrument of claim 1, further comprising an adhesive layer configured to contact a side of the flexible circuit and adapted to adhere the flexible circuit to a portion of the elongated body.

8. The surgical instrument of claim 7, wherein the flexible circuit and the adhesive layer have a combined thickness of 0.10-0.12 mm.

9. The surgical instrument of claim 1 wherein a portion of the elongated body is malleable such that the portion of the elongated body is capable of being bent into a plurality of shapes; and
wherein the flexible circuit is adhered to a cylindrical outer surface of the elongated body and is configured to change shape in response to bending of the portion of the elongated body.

10. The surgical instrument of claim 1, further comprising an outer polymeric shrink layer covering the elongated body and the flexible circuit, wherein the flexible circuit is moveable captured between the outer polymeric shrink layer and the elongated body.

11. The surgical instrument of claim 1, wherein the tracking device includes a plurality of tracking coils configured to nest around a cylindrical surface of the elongated body.

12. The surgical instrument of claim 11, wherein:
the plurality of tracking coils includes three coil assemblies;
each of the coil assemblies has a respective pair of lead wires coupled to a respective pair of traces of the flexible circuit; and
one of the pairs of traces comprises the first trace and the second trace.

13. The surgical instrument of claim 1, wherein the elongated body is tubular-shaped and is a catheter, a cannula, or an endoscope.

14. The surgical instrument of claim 1, wherein the flexible circuit is void of a coil.

15. The surgical instrument of claim 1, wherein the flexible circuit extends from a handle of the surgical instrument to an annular recess area at a distal end of the body.

16. The surgical instrument of claim 1, further comprising:
a sleeve distal to the body and having a proximal end and a distal end, wherein the proximal end of the sleeve is adjacent to and not in contact with the distal end of the body;
a tracking assembly adapted to cooperate with a navigation system to track a distal tip of the surgical instrument, wherein the tracking assembly comprises a printed circuit board and a coil, and wherein the coil is mounted on the sleeve, and wherein the printed circuit board wraps around the distal end of the body and connects to the flexible circuit; and
an insert received in the sleeve and the distal end of the body.

17. The surgical instrument of claim 16, wherein:
the printed circuit board is connected to the flex circuit by a first wire; and
the coil is connected to the printed circuit board by a second wire.

18. The surgical instrument of claim 1, further comprising a second flexible circuit extending from the proximal end to the distal end of the elongated body,
wherein the second flexible circuit comprises a third trace and a fourth trace, has a sinusoidal periphery, and is braided with the first flexible circuit.

19. The surgical instrument of claim 1, wherein the second portion of the first trace crosses over the second portion of the second trace.

20. The surgical instrument of claim 1, wherein:
the first trace includes a plurality of segments;
the plurality of segments include first segments and second segments;
the first segments are on the first side of the base layer;
the second segments are on the second side of the base layer;
each of the first segments is connected to an adjacent one or more of the second segments by one or more of a plurality of vias; and
the plurality of vias extend through the base layer.

21. The surgical instrument of claim 20, wherein:
the second trace includes a second plurality of segments;
the second plurality of segments include third segments and fourth segments;
the third segments are on the second side of the base layer opposite respectively the first segments;
the fourth segments are on the first side of the base layer opposite respectively the second segments; and
each of the third segments is connected to an adjacent one or more of the fourth segments by one or more of the plurality of vias.

22. The surgical instrument of claim 21, wherein:
the first segments and the third segments extend parallel to each other between respective ones of the plurality of vias; and
the second segments and the fourth segments extend parallel to each other between respective ones of the plurality of vias.

23. The surgical instrument of claim 21, wherein, between pairs of the plurality of vias, the first segments, the second segments, the third segments, and the fourth segments extend parallel to a same line except for in areas of the plurality of vias.

24. The surgical instrument of claim 1, further comprising a third trace and a fourth trace extending from the distal end to the proximal end of the elongated body, wherein:
a first portion of the second trace extends parallel to the first portion of the first trace and is on an opposite side of the base layer than the first portion of the first trace;
a first portion of the third trace is on a same side of the base layer as the first portion of the first trace;
a first portion of the fourth trace is on a same side of the base layer as the first portion of the second trace;
the first portion of the fourth trace extends parallel to the first portion of the third trace and is on an opposite side of the base layer than the first portion of the third trace; and
the first portion of the first trace and the first portion of the second trace crossover the first portion of the third trace and the first portion of the fourth trace.

25. The surgical instrument of claim 24, wherein:
a second portion of the second trace extends parallel to the second portion of the first trace and is on an opposite side of the base layer than the second portion of the first trace;
a second portion of the third trace is on a same side of the base layer as the second portion of the first trace;
a second portion of the fourth trace is on a same side of the base layer as the second portion of the second trace;
the second portion of the fourth trace extends parallel to the second portion of the third trace and is on an opposite side of the base layer than the second portion of the third trace; and
the second portion of the first trace and the second portion of the second trace crossover the second portion of the third trace and the second portion of the fourth trace.

26. A surgical instrument, comprising:
an elongated body having a proximal end and a distal end, wherein the elongated body is formed such that the elongated body is capable of being bent between the proximal end and the distal end from a first configuration to a second configuration;
a tracking device coupled to the distal end; and
a flexible circuit disposed adjacent the elongated body, wherein
the flexible circuit has a sinusoidal periphery, extends from the proximal end to the distal end of the elongated body, and has a base layer and a pair of traces,
a first trace of the pair of traces includes first portions and second portions,
the first portions of the first trace are connected to the second portions of the first trace by vias,
each of the vias extend through the base layer,
the first portions of the first trace is on a first side of the base layer,
the second portions of the first trace is on a second side of the base layer,
first portions of a second trace of the pair of traces is on the first side of the base layer,
second portions of the second trace is on the second side of the base layer,
the pair of traces is configured to conform to the first configuration and the second configuration such that the pair of traces does not break during the bending of the elongated body,
the pair of traces electrically connect the tracking device to a navigation system, and
the tracking device is used to track the distal end of the elongated body.

27. The surgical instrument of claim 26, wherein:
the tracking device includes at least two coil assemblies; and
each of the coil assemblies is coupled to the elongated body and is adjacent a distal tip of the surgical instrument.

28. The surgical instrument of claim 27, wherein the at least two coil assemblies are orientated in a non-parallel configuration relative to each other.

29. The surgical instrument of claim 26, further comprising an insulative layer formed over the plurality of traces to isolate the plurality of traces from an external environment, wherein:
the first portions of the first trace extend parallel to and on an opposite side of the base layer as first portions of the second trace;
the base layer, the plurality of traces and the insulative layer form the flexible circuit; and
the base layer and the insulative layer have material properties and a thickness to facilitate the flexible circuit being flexible to conform to an exterior surface of the elongated body.

30. The surgical instrument of claim 29, wherein the second portions of the first trace are formed on an opposite side of the base layer than second portions of the second trace.

31. The surgical instrument of claim 26, further comprising an outer polymeric shrink fit layer covering a portion of the elongated body and the flexible circuit.

32. The surgical instrument of claim 26, wherein the pair of traces form a twisted pair.

33. The surgical instrument of claim 26, wherein:
the first portions of the second trace are connected to the second portions of the second trace by second vias; and
each of the second vias extends through the base layer.

34. The surgical instrument of claim 33, wherein the first trace and the second trace form a twisted pair.

35. A surgical instrument, comprising:
an elongated tubular body having a proximal end and a distal end, wherein the elongated tubular body has an inner diameter defining a first internal flow passage between the proximal end and the distal end, and wherein the elongated tubular body is deformable to be bent between the proximal end and the distal end from a first configuration to a second configuration;
a tracking device coupled to the elongated tubular body and is adjacent to the distal end, wherein
the tracking device is electrically connected to a navigation system and is used to track a distal end of the surgical instrument,
the tracking device includes a flexible circuit and a plurality of coil assemblies,
the flexible circuit has a sinusoidal periphery and comprises a base layer, a plurality of traces, and a plurality of lead wires,
the plurality of traces comprise a first trace and a second trace,
each of the plurality of traces has a first portion formed on a first side of the base layer and a second portion formed on an opposite second side of the base layer,
the first portion of the first trace (i) is positioned opposite to the first portion of the second trace and (ii) is on an opposite side of the base layer than the first portion of the second trace,
the second portion of the first trace (i) is positioned opposite to the second portion of the second trace, and (ii) is on an opposite side of the base layer than the second portion of the second trace, and
the plurality of lead wires are connected respectively to the plurality of traces; and
an insulative layer formed over the plurality of traces to isolate the traces from an external environment,
wherein the base layer and the insulative layer include material properties and have a thickness to facilitate the flexible circuit being flexible such that the flexible circuit is adapted to conform to an exterior surface of the elongated tubular body.

36. The surgical instrument of claim 35, wherein the plurality of traces form a twisted pair.

37. The surgical instrument of claim 35, further comprising an outer polymeric shrink fit layer covering a portion of the elongated body and the flexible circuit.

38. The surgical instrument of claim 35, wherein each of the plurality of coil assemblies is coupled to the flexible circuit at predetermined locations between the proximal end and the distal end.

39. The surgical instrument of claim 35, wherein the flexible circuit protrudes from a surface of the elongated body less than 0.08 mm and provides a uniform outer surface.

40. The surgical instrument of claim 35, wherein the flexible circuit is void of a coil and extends from the proximal end to the distal end of the elongated tubular body.

41. The surgical instrument of claim 35, further comprising a set of wires, wherein:
the set of wires connect the coil assemblies to a printed circuit board; and
the lead wires connect the printed circuit board to the plurality of traces.

* * * * *

UNITED STATES PATENT AND TRADEMARK OFFICE
CERTIFICATE OF CORRECTION

| | | |
|---|---|---|
| PATENT NO. | : 9,226,689 B2 | Page 1 of 1 |
| APPLICATION NO. | : 13/751032 | |
| DATED | : January 5, 2016 | |
| INVENTOR(S) | : Brad Jacobsen et al. | |

It is certified that error appears in the above-identified patent and that said Letters Patent is hereby corrected as shown below:

Title page, (*) Notice: line 3, after "days.", insert --This patent is subject to a terminal disclaimer.--

Signed and Sealed this
Nineteenth Day of April, 2016

Michelle K. Lee
*Director of the United States Patent and Trademark Office*